(12) United States Patent
Gubler et al.

(10) Patent No.: US 7,868,030 B2
(45) Date of Patent: Jan. 11, 2011

(54) FBPASE INHIBITORS FOR DIABETES

(75) Inventors: Marcel Gubler, Arlesheim (CH); Wolfgang Haap, Loerrach (DE); Paul Hebeisen, Basel (CH); Eric A. Kitas, Aesch BL (CH); Bernd Kuhn, Liestal (CH); Rudolf E. Minder, Ettingen (CH); Brigitte Schott, Landser (FR); Hans P. Wessel, Schliengen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 594 days.

(21) Appl. No.: 11/809,043

(22) Filed: May 30, 2007

(65) Prior Publication Data

US 2007/0281979 A1     Dec. 6, 2007

(30) Foreign Application Priority Data

Jun. 1, 2006     (EP)     .................................. 06114848

(51) Int. Cl.
*A61K 31/426*     (2006.01)
*C07D 277/20*     (2006.01)

(52) U.S. Cl. ........................ 514/371; 548/146; 548/190; 548/196; 514/365; 514/370

(58) Field of Classification Search ................. 548/146, 548/190, 193, 196; 514/365, 370, 371
See application file for complete search history.

(56) References Cited

U.S. PATENT DOCUMENTS 6,906,063 B2 *  6/2005  Scarborough et al. .... 514/222.8
7,358,257 B2 *  4/2008  Scarborough et al. .... 514/266.3

FOREIGN PATENT DOCUMENTS

WO     WO 01/47935     7/2001
WO     WO 2004/009118     1/2004

OTHER PUBLICATIONS

Hof et al (1984): STN International HCAPLUS database, (Columbus, Ohio), Accession No. 1984:567016.*
Saijo et al (1989): STN International HCAPLUS database, (Columbus, Ohio), Accession No. 1989:534189.*
Database Chemcats, XP002451585.
Database Chemcats, XP002451586.
Database Chemcats, XP002451587.
Database Chemcats, XP002451588.
Database Chemcats, XP002451589.
Database Chemcats, XP002451590.
Database Chemcats, XP002451591.
Database Chemcats, XP002451592.
Database Chemcats, XP002451593.
Database Chemcats, XP002451594.
Database Chemcats, XP002451595.
Database Chemcats, XP002451596.
Database Chemcats, XP002451597.
Database Chemcats, XP002451598.
Hof H., et al., Arzneimittel Forschung, Drug Research 37(I), No. 3 (1987), XP002128088.
Rusching H., et al., Arzneimittel Forschung, Drug Research, vol. 8, No. 7a, pp. 448-454 (1958), XP009088824.
Husain M. I., et al., Indian Drugs, vol. 24, No. 1, pp. 21-23 (1986).
Van Poelje, P. D. et al, *Diabetes*, (2006) 55(6), 1747-1754.

* cited by examiner

*Primary Examiner*—Golam M Shameem
(74) *Attorney, Agent, or Firm*—George W. Johnston; Dennis P. Tramaloni; Samuel H. Megerditchian

(57) ABSTRACT

Compounds of formula

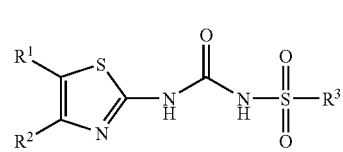

(I)

as well as pharmaceutically acceptable salts and esters thereof, wherein $R^1$ to $R^3$ have the significance given in the application and which can be used in the form of pharmaceutical compositions.

19 Claims, No Drawings

FBPASE INHIBITORS FOR DIABETES

PRIORITY TO RELATED APPLICATION(S)

This application claims the benefit of European Patent Application No. 06114848.2, filed Jun. 1, 2006, which is hereby incorporated by reference in its entirety.

FIELD OF THE INVENTION

The present invention relates to novel compounds useful as FBPase inhibitors. In a preferred embodiment, the invention is concerned with compounds of formula

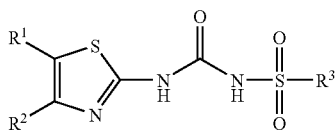

(I)

and pharmaceutically acceptable salts and esters thereof.

All documents cited or relied upon below are expressly incorporated herein by reference.

SUMMARY OF THE INVENTION

In an embodiment of the present invention, provided is a compound of formula (I):

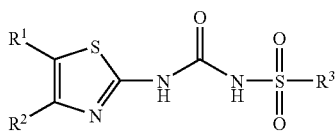

(I)

wherein
$R^1$ is hydrogen, alkyl, cycloalkyl, halogen, haloalkyl, heterocyclyl, heterocyclylalkyl, aralkyl, —S—$R^4$, —O—$R^4$ or nitro;
$R^2$ is hydrogen, alkyl, cycloalkyl, halogen, haloalkyl, alkoxyalkyl, hydroxyalkyl or alkoxycarbonyl;
or $R^1$ and $R^2$ together with the carbon atoms to which they are attached form aryl;
$R^3$ is phenyl, thiazolyl, thiophenyl, pyridinyl, pyrimidinyl, pyradizinyl, oxazoyl or isoxazoyl, wherein phenyl, thiazolyl, thiophenyl, pyridinyl, pyrimidinyl, pyradizinyl, oxazoyl and isoxazoyl are optionally substituted with one to three substituents independently selected from alkyl, cycloalkyl, alkoxy, hydroxy, halogen, haloalkyl, haloalkoxy, aryl, aryloxy, heterocyclyl, heterocyclyloxy, amino, nitro, alkoxyalkyl, hydroxyalkyl, alkoxyalkoxy and hydroxyalkoxy;
$R^4$ is alkyl, cycloalkyl, heterocyclylalkyl, aralkyl or haloalkyl;
and pharmaceutically acceptable salts and esters thereof, with the proviso that $R^1$ and $R^2$ are not both at the same time hydrogen and, wherein
N-((2-benzothiazolylamino)carbonyl)-4-methyl-benzenesulfonamide;
N-((2-benzothiazolylamino)carbonyl)-2-methyl-benzenesulfonamide;
N-(((5,6-dimethyl-2-benzothiazolyl)amino)carbonyl)-2-methyl-benzenesulfonamide;
N-(((4-chloro-2-benzothiazolyl)amino)carbonyl)-2-methyl-benzenesulfonamide;
2-methyl-N-(((4-methyl-2-thiazolyl)amino)carbonyl)-benzenesulfonamide;
N-(((6-ethoxy-2-benzothiazolyl)amino)carbonyl)-2-methyl-benzenesulfonamide; and
4-methyl-N-(((4-methyl-2-thiazolyl)amino)carbonyl)-benzenesulfonamide are excluded.

In another embodiment of the present invention, provided is a process for the preparation of a compound of formula I

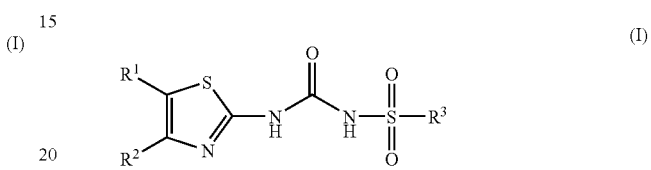

(I)

according to claim 1, comprising one of the following steps:
a) reacting a compound according to formula

$R^3$—$SO_2Cl$      II in the presence of NaOCN and a compound of formula

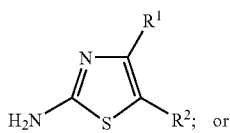

III or b) reacting a compound according to formula

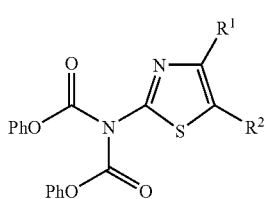

V in the presence of a compound of formula

$R^3SO_2NH_2$      VI;

wherein $R^1$ to $R^3$ are as defined above.

In a further embodiment of the present invention, provided is a pharmaceutical composition, comprising a therapeutically effective amount of a compound according to formula (I) and a therapeutically inert carrier.

In a still another embodiment of the present invention, provided is a method for the treatment of Diabetes Mellitus Type II, Diabetes Mellitus Type I, Diabetes Mellitus Type III, Impaired Fasting Glucose (IFG), Impaired Glucose Tolerance (IGT), diabetic complications or ischaemia, comprising the step of administering a therapeutically effective amount of a compound according to formula (I) to a patient in need thereof.

DETAILED DESCRIPTION

The present invention relates to new chemical compounds that are inhibitors of Fructose-1,6-bisphosphatase (FBPase), a rate-limiting enzyme of gluconeogenesis that is allosterically regulated by AMP and responsible for the hydrolysis of Fructose-1,6-bisphosphate to Fructose-6-phosphate. Compounds of the present invention represent novel FBPase AMP site inhibitors and have valuable pharmacological properties suitable in both human and veterinary medicine.

As inhibitors of FBPase and of the production of Fructose-6-phosphate that is reversibly converted to Glucose-6-phosphate, a metabolite which represents a common precursor for diverse essential metabolic pathways generating glucose, glycogen, ATP, amino acids, nucleotides, NADPH and so forth, compounds of present invention have a large variety of indications related to the management of body homeostasis and the prevention of metabolic dysfunctions.

As inhibitors of FBPase and of gluconeogenesis in the liver, or in other organs capable of producing glucose like kidney or intestine, compounds of the present invention are hypoglycaemic agents and are indicated for the treatment and/or the prophylaxis of disorders of glucose homeostasis, such as Diabetes Mellitus, in particular Type II and Type I Diabetes Mellitus (NIDDM and IDDM), Impaired Fasting Glucose (IFG), Impaired Glucose Tolerance (IGT), and for the prevention of the progression of disorders of the Metabolic Syndrome (MetS, also described as Syndrome X or Insulin Resistance Syndrome) which most important components are insulin resistance (with or without IGT), obesity, dyslipidemia, hypertension, prothrombic and proinflammatory states. As such, compounds of the present invention are also indicated for the prevention and/or the treatment of diabetic complications or diabetic-associated diseases such as cardiomyopathy, macrovascular atherosclerotic disorders, including coronary, cerebrovascular and peripheral artery diseases, microvascular diseases including retinopathy, cataracts, blindness and nephropathy, neuropathy (peripheral neuropathy and sympathetic nerve disorders), diabetic necrosis, infection or depression, and so forth.

In addition, as inhibitors of FBPase that cause the accumulation of Fructose-1,6-bisphosphate capable for increasing the glycolytic production of ATP, compounds of the present invention have cytoprotective effects as anti-ischaemic agents and are useful for preventing ischaemia-induced tissue damage. Therefore, compounds of the present invention can be used in a variety of ischaemic and inflammatory conditions where acute management of tissue injury could be beneficial such as surgical trauma, myocardial infarction, congestive heart failure, stroke, sickle cell disease, and so forth, and have further utility in cardioprotection, in improving cardiac function and tolerance to exercise, in improving red-blood cells and pulmonary endothelial functions, in organ preservation in transplants, and so forth. As such, compounds of the present invention can also be used to treat asthma attacks, hypertension, atheriosclerosis and so forth, and in the management of certain excess glycogen storage diseases such as McArdle disease (GSD-Type V) and others.

Also as inhibitors of FBPase, and thereby of the production from the gluconeogenic pathway of Fructose-6-phosphate and Glucose-6-phosphate that serve as precursors for other pathways of hexose metabolism (e.g. synthesis of amino-sugars/hexosamines that are used for the biosynthesis of glycoproteins, glycosphingolipids or glycosaminoglycans, and uronic acid pathway that leads to glucuronate, a precursor of proteoglycans and conjugated glucuronides, and so forth), or for the pentose phosphate pathway (PPP, also called phosphogluconate pathway) which provides the carbon source for common aromatic biosynthetic pathways (nucleotides and amino-acids synthesis) and generates NADPH for reductive biosyntheses (lipogenesis, steroidogenesis), compounds of the present invention can have further utility in the prevention and/or the management of a large set of diseases including obesity, atherosclerosis, inflammation, Alzheimer disease, cancer or respiratory disorders such as excess mucus production and allergic asthma, excess surfactant synthesis, cystic fibrosis, and so forth.

Furthermore, compounds of the present invention can be used in any disease, syndrome, symptom or organ malfunction found associated with increased expression and/or activity of one or another FBPase isoform, at the obvious exception of certain deficiencies where FBPase upregulation might be beneficial for ensuring normal body function, e.g. certain glycogen storage diseases, such as GSD-Type 0 (glycogen synthase deficiency).

The compounds of formula I and their pharmaceutically acceptable salts and esters are novel and have valuable pharmacological properties. In particular they are FBPase inhibitors and can be used in the prophylaxis and/or treatment of Diabetes Mellitus such as Type I, Type II and Type III Diabetes, Impaired Fasting Glucose (IFG), Impaired Glucose Tolerance (IGT), Metabolic Syndrome, insulin resistance, dyslipidemia, obesity, hypertension, atherosclerosis, diabetic complications, inflammation, respiratory diseases or ischaemia. Preferred is the prophylaxis and/or prevention of progression and/or treatment of Diabetes Mellitus Type II, Diabetes Mellitus Type I, Diabetes Mellitus Type III, Impaired Fasting Glucose (IFG), Impaired Glucose Tolerance (IGT), Metabolic Syndrome, diabetic complications and ischaemia. Particularly preferred is the prophylaxis and/or treatment of Diabetes Mellitus Type II and Diabetes Mellitus Type I.

Embodiments of the present invention are the compounds of formula I and their aforementioned salts and esters per se and their use as therapeutically active substances, a process for the manufacture of the said compounds, intermediates, pharmaceutical compositions, medicaments containing the said compounds, their pharmaceutically acceptable salts and esters, the use of the said compounds, esters and salts for the prophylaxis and/or therapy of illnesses, especially in the treatment and/or prophylaxis of Diabetes Mellitus Type II, Diabetes Mellitus Type I, Diabetes Mellitus Type III, Impaired Fasting Glucose (IFG), Impaired Glucose Tolerance (IGT), diabetic complications or ischaemia, particularly Diabetes Mellitus Type II and Diabetes Mellitus Type I The compounds of the present invention can be combined with one or more additional active substances indicated for the management of human and veterinary homeostasis in any suitable ratio. Such substances may be insulin sensitizers such as peroxisome proliferator-activated receptor modulators (PPAR alpha, gamma, delta agonists, particularly with thiazolinediones such as rosiglitazone and pioglitazone), insulin secretagogues (sulfonylureas such as glyburide, glimepiride and glipizide, and non-sulfonylurea secretagogues such as the meglitinides repaglinide and nateglinide), insulin, metformin, alpha-glucosidase inhibitors (e.g. acarbose, miglitol), glucagon-like peptide (GLP-1) analogues (e.g. exenatide), dipeptidyl peptidase-IV (DPP-IV) inhibitors, glycogen phosphorylase inhibitors, glycogen synthase kinase-3 inhibitors, 11β-hydroxysteroid dehydrogenase-1 inhibitors, carnitine palmitoyltranferase-1 inhibitors, glucocorticoid receptor antagonists, glucagon receptor antagonists, Adenosine ($A_{2B}$) receptor agonists, amylin agonists (e.g. pramlintide), lipase inhibitor (e.g. orlistat), or any other synthetic or natural substance presenting valuable pharmacological properties useful for the treatment and/or the prevention of metabolic dysfunctions.

In the present description the term "alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl", alone or in combination, signifies a cycloalkyl ring with 3 to 8 carbon atoms and preferably a cycloalkyl ring with 3 to 6 carbon atoms. Examples of $C_3$-$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec. butoxy and tert.butoxy, preferably methoxy and ethoxy and most preferred methoxy.

The term "haloalkyl", alone or in combination, signifies an alkyl group as previously defined, wherein one to five hydrogen atoms are substituted by halogen, preferably fluoro. Preferred examples are pentafluoroethyl and particularly trifluoromethyl and difluoromethyl.

The term "haloalkoxy", alone or in combination, signifies a group of the formula haloalkyl-O— in which the term "haloalkyl" is defined as before.

The term "hydroxyalkyl", alone or in combination, signifies an alkyl group as defined before, wherein one or more hydrogen atoms, preferably one hydrogen atom is replaced by a hydroxy group. Examples of hydroxyalkyl are hydroxymethyl and hydroxyethyl.

The term "aryl", alone or in combination, signifies a phenyl or naphthyl group, preferably a phenyl group which optionally carries one or more substituents, preferably one to three, each independently selected from halogen, trifluoromethyl, trifluoromethoxy, amino, alkyl, alkoxy, alkylcarbonyl, cyano, carbamoyl, alkoxycarbamoyl, methylendioxy, carboxy, alkoxycarbonyl, aminocarbonyl, alkyaminocarbonyl, dialkylaminocarbonyl, hydroxy, nitro, alkyl-$SO_2$—, amino-$SO_2$—, cycloalkyl and the like. Examples are phenyl or naphthyl, particularly phenyl optionally substituted with one to three, preferably one or two substituents independently selected from alkyl, halogen, alkoxy, trifluoromethoxy, nitro and trifluoromethyl. Preferred examples are phenyl or phenyl substituted with one to three, preferably one or two substituents independently selected from alkyl, halogen and alkoxy.

The term "aryloxy", alone or in combination, signifies an aryl-O— group in which the term "aryl" has the previously given significance.

The term "alkoxyalkyl", alone or in combination, signifies an alkyl group as defined before, wherein one or more hydrogen atoms, preferably one hydrogen atom is replaced by an alkoxy group as defined before. Examples of alkoxyalkyl are methoxymethyl and methoxyethyl.

The term "alkoxycarbonyl", alone or in combination, signifies an alkoxy-CO— group in which the term "alkoxy" has the previously given significance.

The term "alkoxyalkoxy", alone or in combination, signifies an alkoxy group as defined before, wherein one or more hydrogen atoms, preferably one hydrogen atom is replaced by an alkoxy group as defined before. Examples of alkoxyalkoxy are methoxymethoxy and methoxyethoxy.

The term "hydroxyalkoxy", alone or in combination, signifies an alkoxy group as defined before, wherein one or more hydrogen atoms, preferably one hydrogen atom is replaced by an hydroxy group. An example of hydroxyalkoxy is hydroxyethoxy.

The term "heterocyclyl", alone or in combination signifies a saturated, partially unsaturated or aromatic 5- to 10-membered heterocycle which contains one or more hetero atoms selected from nitrogen, oxygen and sulphur. If desired, it can be substituted on one or more carbon atoms e.g. by halogen, alkyl, alkoxy, oxo etc. and/or on a secondary nitrogen atom (i.e. —NH—) by alkyl, cycloalkyl, aralkoxycarbonyl, alkanoyl, phenyl or phenylalkyl or on a tertiary nitrogen atom (i.e. =N—) by oxido, with halogen, alkyl, cycloalkyl and alkoxy being preferred. Examples of such heterocyclyl groups are pyrrolidinyl, piperidinyl, piperazinyl, morpholinyl, thiomorpholinyl, pyrazoyl, imidazoyl (e.g. imidazol-4-yl and 1-benzyloxycarbonyl-imidazol-4-yl), pyrazoyl, pyridyl, pyrazinyl, pyrimidinyl, hexahydro-pyrimidinyl, furyl, thienyl, thiazolyl, oxazolyl, indolyl (e.g. 2-indolyl), quinolyl (e.g. 2-quinolyl, 3-quinolyl and 1-oxido-2-quinolyl), isoquinolyl (e.g. 1-isoquinolyl and 3-isoquinolyl), tetrahydroquinolyl, 1,2,3,4-tetrahydroisoquinolyl and quinoxalinyl. Preferred are oxazolyl, thienyl, pyrazolyl, thiazolyl, 1,2,3-thiadiazolyl and pyrrolidinyl, wherein oxazolyl, thienyl, pyrazolyl, thiazolyl, 1,2,3-thiadiazolyl and pyrrolidinyl are optionally substituted with one to three substituents, preferably one or two substituents independently selected from alkyl, halogen and cycloalkyl, particularly cyclohexyl.

The term "heterocyclylalkyl", alone or in combination, signifies the heterocyclyl-alkyl group, wherein the terms "heterocyclyl" and "alkyl" are as previously defined.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substituents together forming a ring, such as, for example, —$NH_2$, methylamino, ethylamino, dimethylamino, diethylamino, methyl-ethylamino, pyrrolidin-1-yl or piperidino etc., preferably primary amino, dimethylamino and diethylamino and particularly dimethylamino.

The term "halogen", alone or in combination, signifies fluorine, chlorine, bromine or iodine and preferably fluorine, chlorine or bromine.

The term "carbonyl", alone or in combination, signifies the —C(O)— group.

The term "aralkyl", alone or in combination, signifies the aryl-alkyl group, wherein the terms "aryl" and "alkyl" are as previously defined. Preferred is benzyl.

The term "oxy", alone or in combination, signifies the —O— group.

The term "hydroxy", alone or in combination signifies the group —OH.

The term "nitro", alone or in combination signifies the —$NO_2$ group.

The term "cyano", alone or in combination signifies the group —CN.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. A preferred pharmaceutically acceptable salt of compounds of formula I is the sodium salt.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Pharmaceutically acceptable esters" means that compounds of general formula (I) may be derivatized at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The compounds of formula I can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

Preferred are the compounds of formula I and pharmaceutically acceptable salts thereof, particularly the compounds of formula I.

Further preferred are the compounds of formula

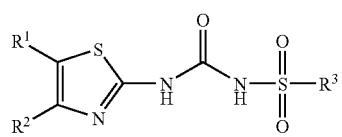

wherein
R$^1$ is hydrogen, alkyl, cycloalkyl, halogen, haloalkyl, heterocyclyl, heterocyclylalkyl, aralkyl, —S—R$^4$ or —O—R$^4$;
R$^2$ is hydrogen, alkyl, cycloalkyl, halogen or haloalkyl;
or R$^1$ and R$^2$ together with the carbon atoms to which they are attached form aryl;

R$^3$ is phenyl, thiazolyl, thiophenyl, pyridinyl, pyrimidinyl, pyradizinyl, oxazoyl or isoxazoyl, wherein phenyl, thiazolyl, thiophenyl, pyridinyl, pyrimidinyl, pyradizinyl, oxazoyl and isoxazoyl are optionally substituted with one to three substituents independently selected from alkyl, cycloalkyl, alkoxy, hydroxy, halogen, haloalkyl, haloalkoxy, aryl, aryloxy, heterocyclyl, heterocyclyloxy, amino and nitro;
R$^4$ is alkyl, cycloalkyl, heterocyclylalkyl or aralkyl;
and pharmaceutically acceptable salts and esters thereof, with the proviso that R$^1$ and R$^2$ are not both at the same time hydrogen and, wherein
N-((2-benzothiazolylamino)carbonyl)-4-methyl-benzenesulfonamide;
N-((2-benzothiazolylamino)carbonyl)-2-methyl-benzenesulfonamide;
N-(((5,6-dimethyl-2-benzothiazolyl)amino)carbonyl)-2-methyl-benzenesulfonamide;
N-(((4-chloro-2-benzothiazolyl)amino)carbonyl)-2-methyl-benzenesulfonamide;
2-methyl-N-(((4-methyl-2-thiazolyl)amino)carbonyl)-benzenesulfonamide;
N-(((6-ethoxy-2-benzothiazolyl)amino)carbonyl)-2-methyl-benzenesulfonamide; and
4-methyl-N-(((4-methyl-2-thiazolyl)amino)carbonyl)-benzenesulfonamide are excluded.

Further preferred are compounds of formula I, wherein R$^1$ is hydrogen, methyl, halogen, thienyl or —S—R$^4$. Particularly preferred are those compounds of formula I, wherein R$^1$ is bromo.

Also preferred are those compounds according to formula I, wherein R$^1$ is nitro.

Moreover, preferred are the compounds of formula I, wherein R$^2$ is hydrogen, methyl, or halogen. Particularly preferred are those, wherein R$^2$ is hydrogen.

Further preferred are those compounds of formula I, wherein R$^2$ alkoxyalkyl, hydroxyalkyl or alkoxycarbonyl.

Additionally preferred are the compounds of formula I, wherein R$^1$ and R$^2$ together with the carbon atoms to which they are attached form phenyl.

Another preferred aspect of the present invention are compounds according to formula I, wherein R$^3$ is phenyl, thiophenyl or pyridinyl, wherein phenyl, thiophenyl and pyridinyl are optionally substituted with one to three substituents, preferably one or two substituents independently selected from alkyl, cycloalkyl, halogen, haloalkoxy, aryloxy, dichloro-methyl-1H-pyrazolyl)oxy, methylthiazolyl, cyclohexyl-methyl-oxazolyl, oxazolyl, thiadiazolyl, methyloxazolyl, methylpyrrolidinyl, (methoxymethyl)-pyrrolidinyl, (methylethyl)-pyrrolidinyl and methoxypyridinyl.

Further preferred are those compounds according to formula I, wherein R$^3$ is phenyl, thiophenyl or pyridinyl, wherein phenyl, thiophenyl and pyridinyl are optionally substituted with one to three substituents, particularly one or two substituents independently selected from alkyl, cycloalkyl, halogen, haloalkoxy, aryloxy, 3,4-dichloro-1-methyl-1H-pyrazol-5-yl)oxy, 2-methyl-4-thiazolyl, 4-cyclohexyl-2-methyl-5-oxazolyl, oxazolyl, 1,2,3-thiadiazol-4-yl, 4-methyl-5-oxazolyl, 2-methyl-1-pyrrolidinyl, 2-(methoxymethyl)-1-pyrrolidinyl, 2-(1-methylethyl)-1-pyrrolidinyl and 6-methoxypyridin-3-yl.

Particularly preferred are the compounds of formula I, wherein R$^3$ is phenyl, thiophenyl or pyridinyl, wherein phenyl, thiophenyl and pyridinyl are optionally substituted with one to three substituents independently selected from alkyl, cyclopropyl, halogen, haloalkoxy, phenyl, difluorophenyl, methylpenyl, methoxyphenyl, methyloxazolyl and methoxypyridinyl.

Further preferred are compounds of formula I, wherein $R^3$ is phenyl, thiophenyl, pyridinyl or thiazolyl, wherein phenyl, thiophenyl, pyridinyl and thiazolyl are optionally substituted with one to three substituents independently selected from alkyl, cycloalkyl, halogen, haloalkoxy, alkoxyalkyl, alkoxyalkoxy, aryloxy, dichloro-methyl-1H-pyrazolyl)oxy, methylthiazolyl, cyclohexyl-methyl-oxazolyl, oxazolyl, thiadiazolyl, methyloxazolyl, methylpyrrolidinyl, (methoxymethyl)-pyrrolidinyl, (methylethyl)-pyrrolidinyl, methoxypyridinyl, 6-methoxy-4-methyl-pyridin-3-yl, alkoxy-alkyl-phenyl, alkoxypyridinyl, fluoropyridinyl and methoxy-thiazolyl.

Particularly preferred are compounds of formula I, wherein $R^3$ is phenyl, thiophenyl, pyridinyl or thiazolyl, wherein phenyl, thiophenyl, pyridinyl and thiazolyl are optionally substituted with one to three substituents independently selected from alkyl, cycloalkyl, halogen, haloalkoxy, alkoxyalkyl, alkoxyalkoxy, aryloxy, 3,4-dichloro-1-methyl-1H-pyrazol-5-yl)oxy, 2-methyl-4-thiazolyl, 4-cyclohexyl-2-methyl-5-oxazolyl, oxazolyl, 1,2,3-thiadiazol-4-yl, 4-methyl-5-oxazolyl, 2-methyl-1-pyrrolidinyl, 2-(methoxymethyl)-1-pyrrolidinyl, 2-(1-methylethyl)-1-pyrrolidinyl, 6-methoxypyridin-3-yl, 6-methoxy-4-methylpyridin-3-yl, 4-methoxy-2-methylphenyl, methoxy-pyridinyl, 5-isobutyl-4-methylthiophenyl, 6-fluoropyridin-3-yl, 5-fluoropyridin-3-yl and 2-methoxy-1,3-thiazol-4-yl.

Another preferred aspect of the present invention are the compounds of formula I, wherein $R^4$ is alkyl, alkyloxazolyl-methyl or phenylmethyl. Particularly preferred are those, wherein $R^4$ is methyl or ((1,1-dimethylethyl)-2-oxazolyl)methyl.

Preferred compounds of formula I are those, wherein $R^4$ is haloalkyl.

Examples of preferred compounds of formula (I) are:
1. N-[(5-bromo-1,3-thiazol-2-yl)carbamoyl]-3(difluoromethoxy)benzenesulfonamide;
2. 4-bromo-N-[(5-bromo-1,3-thiazol-2-yl)carbamoyl]-5-chlorothiophene-2-sulfonamide;
3. N-[(5-bromo-1,3-thiazol-2-yl)carbamoyl]-3,4-dichlorobenzenesulfonamide;
4. N-[(5-bromo-1,3-thiazol-2-yl)carbamoyl]-4-chloro-3-methylbenzenesulfonamide;
5. N-[(5-bromo-1,3-thiazol-2-yl)carbamoyl]-3-methylbenzenesulfonamide;
N-[(5-bromo-1,3-thiazol-2-yl)carbamoyl]-2',4'-difluorobiphenyl-4-sulfonamide;
6. N-[(5-bromo-1,3-thiazol-2-yl)carbamoyl]-3-chlorobenzenesulfonamide;
7. N-[(5-bromo-1,3-thiazol-2-yl)carbamoyl]-4,5-dichlorothiophene-2-sulfonamide;
8. N-[(5-bromo-1,3-thiazol-2-yl)carbamoyl]-4-(2-chlorophenoxy)-benzenesulfonamide;
9. N-[(5-bromo-1,3-thiazol-2-yl)carbamoyl]-3,5-dimethylbenzenesulfonamide;
10. N-[(5-bromo-1,3-thiazol-2-yl)carbamoyl]-4-[(3,4-dichloro-1-methyl-1H-pyrazol-5-yl)oxy]benzenesulfonamide;
11. N-[(5-bromo-1,3-thiazol-2-yl)carbamoyl]-4-(2-methyl-1,3-thiazol-4-yl)benzenesulfonamide;
12. N-[(5-bromo-1,3-thiazol-2-yl)carbamoyl]-5-methylthiophene-2-sulfonamide;
13. N-[(5-bromo-1,3-thiazol-2-yl)carbamoyl]-5-phenylthiophene-2-sulfonamide;
14. N-[(5-bromo-1,3-thiazol-2-yl)carbamoyl]biphenyl-4-sulfonamide;
15. N-[(5-bromo-1,3-thiazol-2-yl)carbamoyl]-5-chlorothiophene-2-sulfonamide;
16. N-[(5-bromo-1,3-thiazol-2-yl)carbamoyl]-3-fluorobenzenesulfonamide;
17. N-[(5-bromo-1,3-thiazol-2-yl)carbamoyl]-3-methoxybenzenesulfonamide;
18. N-[(5-bromo-1,3-thiazol-2-yl)carbamoyl]-2,5-dichlorothiophene-3-sulfonamide;
19. N-[(5-bromo-1,3-thiazol-2-yl)carbamoyl]-3,4-difluorobenzenesulfonamide;
20. N-[(5-bromo-1,3-thiazol-2-yl)carbamoyl]-4-methoxybenzenesulfonamide;
21. N-[(5-bromo-1,3-thiazol-2-yl)carbamoyl]-4-chlorobenzenesulfonamide;
22. N-[(5-bromo-1,3-thiazol-2-yl)carbamoyl]-4-(4-cyclohexyl-2-methyl-1,3-oxazol-5-yl)-2-fluorobenzenesulfonamide;
23. N-[(5-bromo-1,3-thiazol-2-yl)carbamoyl]-4-(2-methoxyphenoxy)-benzenesulfonamide;
24. N-[(5-bromo-1,3-thiazol-2-yl)carbamoyl]-3-nitrobenzenesulfonamide;
25. N-[(5-bromo-1,3-thiazol-2-yl)carbamoyl]-4-(1,3-oxazol-5-yl)benzenesulfonamide;
26. N-[(5-bromo-1,3-thiazol-2-yl)carbamoyl]-3,5-difluorobenzenesulfonamide;
27. N-[(5-bromo-1,3-thiazol-2-yl)carbamoyl]-4-fluorobenzenesulfonamide;
28. N-[(5-bromo-1,3-thiazol-2-yl)carbamoyl]-4-methylbenzenesulfonamide;
29. N-[(5-bromo-1,3-thiazol-2-yl)carbamoyl]-4-ethylbenzenesulfonamide;
30. N-[(5-bromo-1,3-thiazol-2-yl)carbamoyl]benzenesulfonamide;
31. N-[(5-bromo-1,3-thiazol-2-yl)carbamoyl]-4-(1,2,3-thiadiazol-4-yl)benzenesulfonamide;
32. N-[(5-bromo-1,3-thiazol-2-yl)carbamoyl]-3-(trifluoromethoxy)-benzenesulfonamide;
33. N-[(5-{[(5-tert-butyl-1,3-oxazol-2-yl)methyl]thio}-1,3-thiazol-2-yl)carbamoyl]-3-methylbenzenesulfonamide;
34 3-methyl-N-{[5-(2-thienyl)-1,3-thiazol-2-yl]carbamoyl}benzenesulfonamide;
35. N-[(4-chloro-1,3-thiazol-2-yl)carbamoyl]-3-methylbenzenesulfonamide;
36. N-{[5-(benzylthio)-1,3-thiazol-2-yl]carbamoyl}-3-methylbenzenesulfonamide;
37. N-(1,3-benzothiazol-2-ylcarbamoyl)-3-methylbenzenesulfonamide;
38. N-[(4,5-dimethyl-1,3-thiazol-2-yl)carbamoyl]-3-methylbenzenesulfonamide;
39. N-[(5-bromo-1,3-thiazol-2-yl)carbamoyl]-2-ethyl-2'-methylbiphenyl-4-sulfonamide;
40. N-[(5-bromo-1,3-thiazol-2-yl)carbamoyl]-2-ethylbiphenyl-4-sulfonamide;
41. N-[(5-bromo-1,3-thiazol-2-yl)carbamoyl]-2-ethyl-3'-methylbiphenyl-4-sulfonamide;
42. N-[(5-bromo-1,3-thiazol-2-yl)carbamoyl]-2,6-dimethylbiphenyl-4-sulfonamide;
43. N-[(5-bromo-1,3-thiazol-2-yl)carbamoyl]-4-(4-methyl-1,3-oxazol-5-yl)benzenesulfonamide;
44. N-[(5-bromo-1,3-thiazol-2-yl)carbamoyl]-5-chloro-6-(2-methylpyrrolidin-1-yl)pyridine-3-sulfonamide;
45. N-[(5-bromo-1,3-thiazol-2-yl)carbamoyl]-5-chloro-6-[(2S)-2-(methoxymethyl)pyrrolidin-1-yl]pyridine-3-sulfonamide;
46. N-[(5-bromo-1,3-thiazol-2-yl)carbamoyl]-5-chloro-6-(2-isopropylpyrrolidin-1-yl)pyridine-3-sulfonamide;

47. N-[(5-bromo-1,3-thiazol-2-yl)carbamoyl]-3-ethylbenzenesulfonamide;
48. N-[(5-bromo-1,3-thiazol-2-yl)carbamoyl]-3-isopropyl-benzenesulfonamide;
49. N-[(5-bromo-1,3-thiazol-2-yl)carbamoyl]-5-(4-methoxyphenyl)thiophene-2-sulfonamide;
50. N-[(5-bromo-1,3-thiazol-2-yl)carbamoyl]-5-isobutylthiophene-2-sulfonamide;
51. N-[(5-Bromo-1,3-thiazol-2-yl)carbamoyl]-5-(4-methoxyphenyl)-4-methyl-thiophene-2-sulfonamide;
52. N-[(5-Chloro-1,3-thiazol-2-yl)carbamoyl]-3-methylbenzenesulfonamide;
53. 3-Chloro-N-{[5-(methylthio)-1,3-thiazol-2-yl]carbamoyl}benzenesulfonamide;
54. N-[(5-Bromo-1,3-thiazol-2-yl)carbamoyl]-3-cyclopropyl-benzenesulfonamide;
55. N-[(5-Bromo-1,3-thiazol-2-yl)carbamoyl]-2-chlorobenzenesulfonamide; and
56. N-[(5-Bromo-1,3-thiazol-2-yl)carbamoyl]-5-(6-methoxypyridin-3-yl)-4-methylthiophene-2-sulfonamide.

Examples of particularly preferred compounds of formula (I) are:

N-[(5-bromo-1,3-thiazol-2-yl)carbamoyl]-3-(difluoromethoxy)benzenesulfonamide;
4-bromo-N-[(5-bromo-1,3-thiazol-2-yl)carbamoyl]-5-chlorothiophene-2-sulfonamide;
N-[(5-bromo-1,3-thiazol-2-yl)carbamoyl]-3,4-dichlorobenzenesulfonamide;
N-[(5-bromo-1,3-thiazol-2-yl)carbamoyl]-4-chloro-3-methylbenzenesulfonamide;
N-[(5-bromo-1,3-thiazol-2-yl)carbamoyl]-3-methylbenzenesulfonamide;
N-[(5-bromo-1,3-thiazol-2-yl)carbamoyl]-2',4'-difluorobiphenyl-4-sulfonamide;
N-[(5-{[(5-tert-butyl-1,3-oxazol-2-yl)methyl]thio}-1,3-thiazol-2-yl)carbamoyl]-3-methylbenzenesulfonamide;
N-[(5-bromo-1,3-thiazol-2-yl)carbamoyl]-2-ethyl-2'-methylbiphenyl-4-sulfonamide;
N-[(5-bromo-1,3-thiazol-2-yl)carbamoyl]-2-ethylbiphenyl-4-sulfonamide;
N-[(5-bromo-1,3-thiazol-2-yl)carbamoyl]-4-(4-methyl-1,3-oxazol-5-yl)benzenesulfonamide;
N-[(5-bromo-1,3-thiazol-2-yl)carbamoyl]-3-ethylbenzenesulfonamide;
N-[(5-bromo-1,3-thiazol-2-yl)carbamoyl]-5-(4-methoxyphenyl)thiophene-2-sulfonamide;
N-[(5-bromo-1,3-thiazol-2-yl)carbamoyl]-5-isobutylthiophene-2-sulfonamide;
N-[(5-bromo-1,3-thiazol-2-yl)carbamoyl]-5-(4-methoxyphenyl)-4-methyl-thiophene-2-sulfonamide;
N-[(5-chloro-1,3-thiazol-2-yl)carbamoyl]-3-methylbenzenesulfonamide;
3-chloro-N-{[5-(methylthio)-1,3-thiazol-2-yl]carbamoyl}benzenesulfonamide;
N-[(5-bromo-1,3-thiazol-2-yl)carbamoyl]-3-cyclopropylbenzenesulfonamide and
N-[(5-bromo-1,3-thiazol-2-yl)carbamoyl]-5-(6-methoxypyridin-3-yl)-4-methylthiophene-2-sulfonamide.

Further preferred compounds according to formula I are
1. [(5-bromo-1,3-thiazol-2-yl)carbamoyl]-4-chloro-5-(2-methoxyethyl)thiophene-2-sulfonamide;
2. [(5-bromo-1,3-thiazol-2-yl)carbamoyl]-5-(4-methoxy-2-methylphenyl)-4-methylthiophene-2-sulfonamide;
3. [(5-bromo-1,3-thiazol-2-yl)carbamoyl]-4-(6-methoxypyridin-3-yl)-3-methylbenzenesulfonamide;
4. [(5-bromo-1,3-thiazol-2-yl)carbamoyl]-5-isobutyl-4-methylthiophene-2-sulfonamide;
5. methyl-N-({4-methyl-5-[(trifluoromethyl)thio]-1,3-thiazol-2-yl}carbamoyl)benzenesulfonamide;
6. [(5-bromo-1,3-thiazol-2-yl)carbamoyl]-5-(2-methoxyethyl)-4-methylthiophene-2-sulfonamide;
7. [(5-bromo-1,3-thiazol-2-yl)carbamoyl]-4-(6-fluoropyridin-3-yl)-3-methylbenzenesulfonamide;
8. [(5-bromo-1,3-thiazol-2-yl)carbamoyl]-5-(6-fluoropyridin-3-yl)-4-methylthiophene-2-sulfonamide;
9. [(5-bromo-1,3-thiazol-2-yl)carbamoyl]-3-chloro-4-fluorobenzenesulfonamide;
10. N-[(5-bromo-1,3-thiazol-2-yl)carbamoyl]-5-(3-methoxypropyl)-4-methylthiophene-2-sulfonamide;
11. N-[(5-bromo-1,3-thiazol-2-yl)carbamoyl]-4-(2-methoxy-1,3-thiazol-4-yl)-3-methylbenzenesulfonamide;
12. N-[(5-bromo-1,3-thiazol-2-yl)carbamoyl]-4-(5-fluoropyridin-3-yl)-3-methylbenzenesulfonamide;
13. N-[(5-bromo-1,3-thiazol-2-yl)carbamoyl]-5-methoxy-4-methylthiophene-2-sulfonamide;
14. N-[(5-bromo-1,3-thiazol-2-yl)carbamoyl]-5-(2-methoxyethoxy)-4-methylthiophene-2-sulfonamide;
15. N-[(5-bromo-1,3-thiazol-2-yl)carbamoyl]-5-(6-methoxy-4-methylpyridin-3-yl)-4-methylthiophene-2-sulfonamide;
16. N-[(5-bromo-1,3-thiazol-2-yl)carbamoyl]-5-(methoxymethyl)-4-methylthiophene-2-sulfonamide;
17. N-[(5-bromo-4-methyl-1,3-thiazol-2-yl)carbamoyl]-3-methylbenzenesulfonamide;
18. N-[(5-bromo-4-methyl-1,3-thiazol-2-yl)carbamoyl]-3-(difluoromethoxy)benzenesulfonamide;
19. 3-methyl-N-[(4-methyl-5-nitro-1,3-thiazol-2-yl)carbamoyl]benzenesulfonamide;
20. N-{[5-bromo-4-(methoxymethyl)-1,3-thiazol-2-yl]carbamoyl}-3-methylbenzenesulfonamide;
21. ethyl 5-bromo-2-({[(3-methylphenyl)sulfonyl]carbamoyl}amino)-1,3-thiazole-4-carboxylate;
22. N-[(5-methoxy-4-methyl-1,3-thiazol-2-yl)carbamoyl]-3-methylbenzenesulfonamide; and
23. N-{[5-bromo-4-(hydroxymethyl)-1,3-thiazol-2-yl]carbamoyl}-3-methylbenzenesulfonamide.

Further particularly preferred compounds of formula I are
N-[(5-bromo-1,3-thiazol-2-yl)carbamoyl]-5-isobutyl-4-methylthiophene-2-sulfonamide;
N-[(5-bromo-1,3-thiazol-2-yl)carbamoyl]-4-(6-fluoropyridin-3-yl)-3-methylbenzenesulfonamide;
N-[(5-bromo-1,3-thiazol-2-yl)carbamoyl]-5-(3-methoxypropyl)-4-methylthiophene-2-sulfonamide;
N-[(5-bromo-1,3-thiazol-2-yl)carbamoyl]-5-(2-methoxyethoxy)-4-methylthiophene-2-sulfonamide;
N-[(5-bromo-1,3-thiazol-2-yl)carbamoyl]-5-(6-methoxy-4-methylpyridin-3-yl)-4-methylthiophene-2-sulfonamide;
N-[(5-bromo-1,3-thiazol-2-yl)carbamoyl]-5-(methoxymethyl)-4-methylthiophene-2-sulfonamide;
N-[(5-bromo-4-methyl-1,3-thiazol-2-yl)carbamoyl]-3-methylbenzenesulfonamide;
N-[(5-bromo-4-methyl-1,3-thiazol-2-yl)carbamoyl]-3-(difluoromethoxy)benzenesulfonamide;
ethyl 5-bromo-2-({[(3-methylphenyl)sulfonyl]carbamoyl}amino)-1,3-thiazole-4-carboxylate; and
N-[(5-methoxy-4-methyl-1,3-thiazol-2-yl)carbamoyl]-3-methylbenzenesulfonamide.

Processes for the manufacture of compounds of formula I are an embodiment of the invention.

The preparation of compounds of formula I of the present invention may be carried out in sequential or convergent synthetic routes. Syntheses of the invention are shown in the following Schemes. The skills required for carrying out the reaction and purification of the resulting products are known to those persons skilled in the art. The substituents and indices used in the following description of the processes have the significance given above unless indicated to the contrary.

Compounds of formula I can be prepared as shown in Schemes 1-2 and in the preparative examples 1-55. The starting material of formula II are known compounds or may be prepared by methods well known in the art.

Sulfonylurea derivatives of aminothiazoles III were mainly prepared by approaches described in Scheme 1. An aryl or heteroaryl sulfonyl chloride derivative II was converted to an intermediate isocyanate complex following reaction with sodium cyanate in pyridine (Lit.: U.S. Pat. No. 5,550,238). The intermediate was directly reacted with aminothiazoles III to yield inhibitors I. Alternatively, aminothiazole III was reacted with phenyl chloroformate IV in the presence of pyridine to prepare the bis-carbamate derivative V (Lit.: DE 1950). An aryl or heteroaryl sulfonamide VI was then reacted with V in the presence of base such as DBU to yield compounds of type I.

Scheme 2

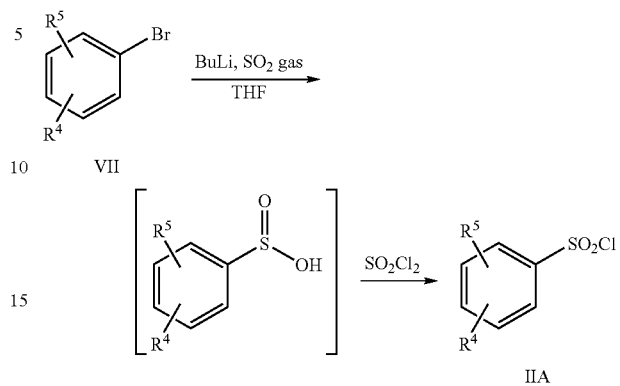

Scheme 1

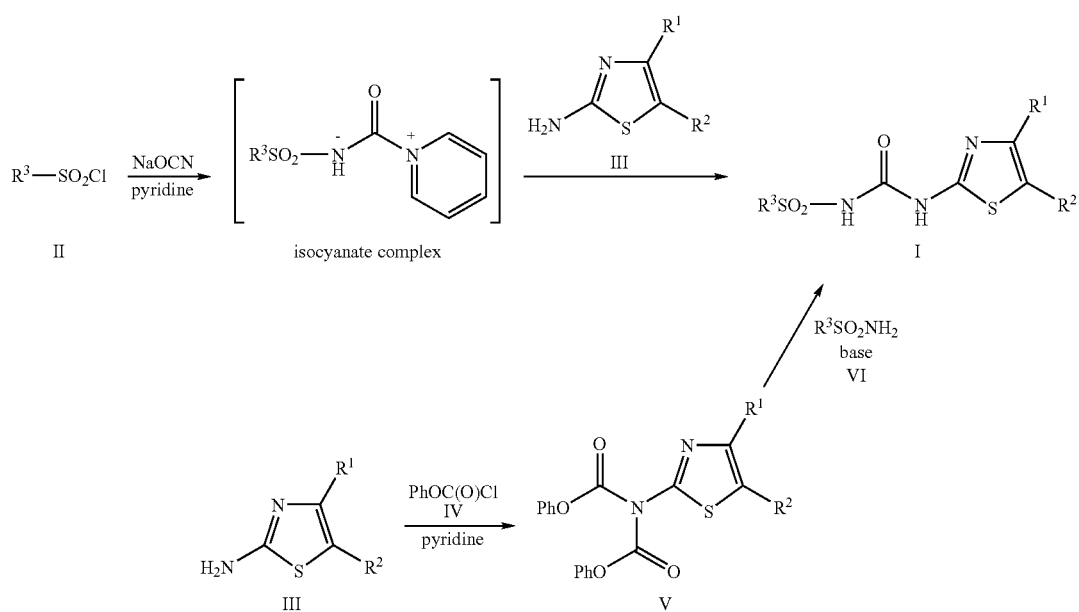

Phenyl sulfonyl chlorides IIA were prepared from the corresponding bromide VII by first, lithium halogen exchange at low temperature in an inert solvent such as THF and trapping the lithiated species with $SO_2$ gas. The resultant intermediate was reacted with a chlorinating reagent such as sulfuryl chloride or N-chlorosuccinimide to prepare IIA. Alternatively, an aryl amine VIII underwent diazotisation with sodium nitrite. The diazonium salt intermediate, in the presence of $SO_2$ gas, copper (I) chloride and in an acidic solution, underwent the Meerwein reaction to yield IIA. A third method employed was the direct reaction of activated phenyl 1× and chlorosulfonic acid. Thiophene sulfonyl chlorides IIB were prepared from thiophene precursors X by reacting with a preformed DMF-$SO_2Cl_2$ complex. Alternatively, lithiation with butyl lithium at low temperature and subsequent reaction with sulfuryl chloride also furnished compounds of type IIB (Scheme 2).

-continued

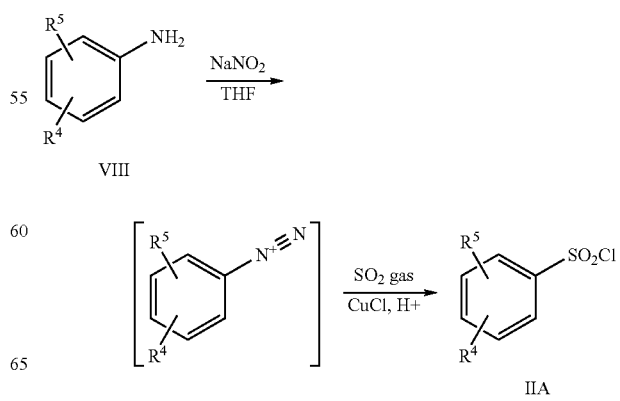

-continued

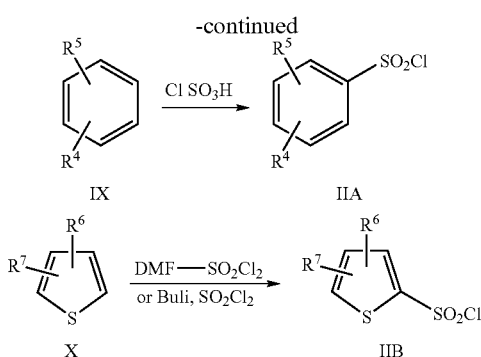

A preferred process for the preparation of a compound of formula

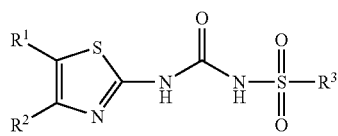

as described before comprises one of the following reactions, wherein $R^1$ to $R^3$ are defined as before
a) reaction of a compound according to formula $$R^3-SO_2Cl \quad \quad II$$

in the presence of NaOCN and a compound of formula

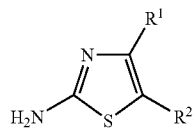

in order to obtain a compound of formula I. Particularly preferred are those reactions according to a) wherein the reaction is performed in the presence of pyridine; or
b) reaction of a compound according to formula

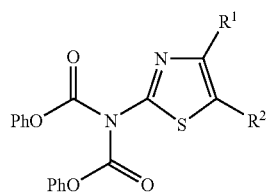

in the presence of a compound of formula $$R^3SO_2NH_2 \quad \quad VI$$

in order to obtain a compound according to formula I. Particularly preferred are those reactions according to b) wherein the reaction is performed in the presence of a base such as e.g. DBU (1,8-diazabicyclo[5.4.0]undec-7-ene).

Preferred intermediates are:
4-(4-cyclohexyl-2-methyl-oxazol-5-yl)-2-fluoro-benzene-sulfonamide;
2-ethyl-2'-methyl-biphenyl-4-sulfonyl chloride;
2-ethyl-biphenyl-4-sulfonyl chloride;
2,6-dimethyl-biphenyl-4-sulfonyl chloride;
4-(4-methyl-oxazol-5-yl)-benzenesulfonyl chloride;
3-ethyl-benzenesulfonyl chloride;
3-isopropyl-benzenesulfonyl chloride;
3-cyclopropyl-benzenesulfonyl chloride;
5-isobutyl-thiophene-2-sulfonyl chloride;
5-(4-methoxy-phenyl)-thiophene-2-sulfonyl chloride;
5-(4-methoxy-phenyl)-4-methyl-thiophene-2-sulfonyl chloride;
5-(6-methoxy-pyridin-3-yl)-4-methyl-thiophene-2-sulfonyl chloride and
5-(6-methoxy-pyridin-3-yl)-4-methyl-thiophene-2-sulfonic acid amide.

The compounds of formula I as described above for use as therapeutically active substance are a further embodiment of the invention.

A further embodiment of the invention are the compounds according to formula I for the preparation of medicaments for the prophylaxis and/or therapy of illnesses which are caused by disorders associated with the enzyme Fructose-1,6-bisphosphatase, preferably Diabetes Mellitus Type II, Diabetes Mellitus Type I, Diabetes Mellitus Type III, Impaired Fasting Glucose (IFG), Impaired Glucose Tolerance (IGT), diabetic complications or ischaemia.

Likewise preferred is a pharmaceutical composition comprising a compound of formula I as described and a therapeutically inert carrier.

A further preferred embodiment of the invention is the use of a compound according to formula I as described for the preparation of medicaments for the treatment and/or prophylaxis of Diabetes Mellitus Type II, Diabetes Mellitus Type I, Diabetes Mellitus Type III, Impaired Fasting Glucose (IFG), Impaired Glucose Tolerance (IGT), diabetic complications or ischaemia and particularly preferred for the treatment and/or prophylaxis of Diabetes Mellitus Type II or Diabetes Mellitus Type I.

A further embodiment of the present invention is a compound according to formula I, when manufactured according to any one of the described processes.

Likewise preferred is a method for the treatment and/or prophylaxis of Diabetes Mellitus Type II, Diabetes Mellitus Type I, Diabetes Mellitus Type III, Impaired Fasting Glucose (IFG), Impaired Glucose Tolerance (IGT), diabetic complications or ischaemia, which method comprises administering an effective amount of a compound of formula I as described. Preferred is this method for the treatment and/or prophylaxis of Diabetes Mellitus Type II or Diabetes Mellitus Type I.

Assay Procedures

FBPase Assay Description:
The following tests were carried out for evaluating the inhibitory activity of the compounds of the present invention against human liver FBPase (Swissprot Data base reference PO9467, entry F16P_HUMAN).

Enzyme preparation: Human liver FBPase cDNA (NM_000507) was purchased from Origene Technologies, Inc, sub-cloned in a vector for expression in *E. Coli.*, and sequenced. Recombinant human liver FBPase (hlFBPase) was purified according to the following protocol that uses heat denaturation similarly to that described by El-Maghrabi et. al. [El- Maghrabi, M. R. et al. "Isolation of a human liver fructose-1,6-bisphosphatase cDNA and expression of the protein in *Escherichia coli*." J Biol Chem 268:9466-9472, 1993.]. Briefly, *E. coli* cells, transiently expressing very high levels of soluble and active human liver FBPase, were suspended in 20 mM Tris-HCl pH 7.5, 1 mM EDTA, 1 mM DTT and were lysed by French press. The soluble extract was heat denatured at 65° C. for 5 min, and insoluble, denatured proteins were removed by centrifugation. The extract was then applied to a BioRad Macro-Prep High Q column equilibrated with 20 mM Tris-HCl pH 7.5, 1 mM EDTA, 1 mM DTT and the flow-through (containing FBPase activity) was collected and applied to a BioRad Macro-Prep HS column equilibrated with 20 mM HEPES pH 7.2, 1 mM DTT. A gradient of increasing NaCl concentration was then applied to the HS column and fractions were collected. Fractions containing active FBPase were pooled and further purified by size exclusion chromatography on a Sephacryl S200 column equilibrated in 20 mM Tris-HCl pH 7.5, 150 mM NaCl, 1 mM EDTA, 1 mM DTT. Purity of the enzyme preparation was >90% as assessed by Mass spectrometry.

In vitro activity: Recombinant human liver FBPase (hlFBPase) activity was assayed through measuring the inorganic phosphate release that results from the hydrolysis of Fructose-1,6-bisphosphate by the enzyme. As described by Baykov A. A. et al. in [Baykov A. A et al., "Malachite Green procedure for orthophosphate determination and its use in alkaline phosphatase-based enzyme immunoassays". Anal. Biochem., 171:266-270, 1988], inorganic phosphate can be readily quantified by spectrophotometry at 620 nm after complexation with ammonium molybdate/malachite green reagent. Enzymatic reaction was carried out with modifications of the procedure described by Wright S. W. et al. [Wright S. W. et al., "Anilinoquinazoline inhibitors of Fructose-1,6-bisphosphatase bind to a novel allosteric site: synthesis, in vitro characterization, and X-ray crystallography". J. Med. Chem. 45:3865-3877, 2002]. Specifically, the reaction was carried out in 96 well plates in a final volume of 100 μl in the presence or in the absence of allosteric inhibitors. Reaction was started adding 25 ng of hlFBPase to the reaction mixture containing 50 mM HEPES-KOH buffer pH 7.2, 2 mM $MgCl_2$, 2 mM EDTA, 1 mM DTT, 50 μM fructose-1,6-bisphosphate and 1% DMSO. After 50 minutes incubation at room temperature, the phosphate released was allowed to form a colored complex for 10 min by adding 150 μl of ammonium molybdate/malachite green reagent containing 0.03% malachite green, 0.2% ammonium molybdate, 0.05% Triton X-100 and 0.7 M $H_2SO_4$ in water that was stirred for 30 min at room temperature and filtered through 0.2 μm filter. Under these conditions, the assay was linear with time and able to detect FBPase inhibition after spectrophotometric read-out at 620 nm.

Results obtained in the assay above using representative compounds of the invention as the test compounds are shown in the following table:

| Compound | FBPase assay $IC_{50}$ (nM) |
| --- | --- |
| Example 5 | 250 |
| Example 52 | 65 |

Compounds as described above have $IC_{50}$ values of 1.0 μM to 1 nM; preferred compounds have $IC_{50}$ values of 500 to 1 nM. More preferred compounds have $IC_{50}$ values of 200 to 1 nM. These results have been obtained by using the foregoing test.

In vivo activity: Glucose lowering activity of representative compounds of the present invention was demonstrated after acute treatment in male adult and diabetic db/db mice. db/db mice (12-20 weeks of age) were purchased from Jackson laboratories and time-course effect of compounds on blood glucose levels was measured from tail vein samplings using fluorometric method (Glucotrend systems (Roche AG)).

The compounds of formula I and their pharmaceutically acceptable salts and esters can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays), as aerosol formulations or rectally (e.g. in the form of suppositories). However, the administration can also be effected parentally, such as intramuscularly or intravenously (e.g. in the form of injection solutions).

The compounds of formula I and their pharmaceutically acceptable salts and esters can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules are, for example, vegetable oils, waxes, fats, semi-solid substances and liquid polyols, etc.

Suitable adjuvants for the production of solutions and syrups are, for example, water, polyols, saccharose, invert sugar, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically acceptable salts can be used e.g. for the prophylaxis and/or treatment of Diabetes Mellitus Type II, Diabetes Mellitus Type I, Diabetes Mellitus Type III, Impaired Fasting Glucose (IFG), Impaired Glucose Tolerance (IGT), diabetic complications or ischaemia. The dosage can vary in wide limits and will, of course, be fitted to the individual requirements in each particular case. In general, in the case of oral administration a daily dosage of about 0.1 mg to 100 mg per kg body weight, preferably about 0.5 mg to 10 mg per kg body weight (e.g. about 300 mg per person), divided into preferably 1-3 individual doses, which can consist, for example, of the same amounts, should be appropriate. It will, however, be clear that the upper limit given above can be exceeded when this is shown to be indicated.

The invention is illustrated hereinafter by Examples, which have no limiting character.

EXAMPLES

Example 1

N-[(5-Bromo-1,3-thiazol-2-yl)carbamoyl]-3-(difluoromethoxy)benzenesulfonamide

The title compound, MS: m/e 429.9 (MH$^+$), was prepared analogously to the procedure described for Example 2, using 3-difluoromethoxy-benzenesulfonyl chloride.
δH (400 MHz; d6-dimethylsulfoxide) 7.84 (1H, d), 7.69-7.73 (2H, m), 7.50-7.54 (2H, m), 7.36 (1H, t)

Example 2

4-Bromo-N-[(5-bromo-1,3-thiazol-2-yl)carbamoyl]-5-chlorothiophene-2-sulfonamide

4-Bromo-5-chloro-thiophene-2-sulfonyl chloride (0.44 g, 1.50 mmol) and pyridine (0.27 ml, 3.40 mmol) were added to a stirred suspension of sodium cyanate (0.14 g, 2.20 mmol) in dry acetonitrile (1 ml) and the mixture stirred at room temperature for 4 hours. 5-Bromo-thiazol-2-ylamine hydrobromide (0.26 g, 1.00 mmol) was added and the reaction stirred for 30 minutes. Water (2 ml) and acetic acid (3 drops) were added. The resulting precipitate was filtered and the solid washed with water, cold methanol and diethyl ether. The solid was dried under reduced pressure to give 4-bromo-N-[(5-bromo-1,3-thiazol-2-yl)carbamoyl]-5-chlorothiophene-2-sulfonamide, 0.29 g (60%), m/e 477.8 (MH$^-$).

Example 3

N-[(5-Bromo-1,3-thiazol-2-yl)carbamoyl]-3,4-dichlorobenzenesulfonamide

The title compound, MS: m/e 427.9 (MH$^-$), was prepared analogously to the procedure described for Example 2, using 3,4-dichloro-benzenesulfonyl chloride.

Example 4

N-[(5-Bromo-1,3-thiazol-2-yl)carbamoyl]-4-chloro-3-methylbenzenesulfonamide

The title compound, MS: m/e 411.9 (MH$^+$), was prepared analogously to the procedure described for Example 2, using 4-chloro-3-methyl-benzenesulfonyl chloride.

Example 5

N-[(5-Bromo-1,3-thiazol-2-yl)carbamoyl]-3-methylbenzenesulfonamide

The title compound, MS: m/e 374.0 (MH$^-$), was prepared analogously to the procedure described for Example 2, using 3-methyl-benzenesulfonyl chloride.

Example 6

N-[(5-Bromo-1,3-thiazol-2-yl)carbamoyl]-2',4'-difluorobiphenyl-4-sulfonamide

The title compound, MS: m/e 475.9 (MH$^+$), was prepared analogously to the procedure described for Example 2, using 2',4'-difluoro-biphenyl-4-sulfonyl chloride.

Example 7

N-[(5-Bromo-1,3-thiazol-2-yl)carbamoyl]-3-chlorobenzenesulfonamide

The title compound, MS: m/e 393.9 (MH$^-$), was prepared analogously to the procedure described for Example 2, using 3-chloro-benzenesulfonyl chloride.

Example 8

N-[(5-Bromo-1,3-thiazol-2-yl)carbamoyl]-4,5-dichlorothiophene-2-sulfonamide

The title compound was prepared analogously to the procedure described for Example 2, using 4,5-dichlorothiophene-2-sulfonyl chloride: δH (400 MHz; d6-dimethylsulfoxide) 7.67 (1H, s), 7.46 (1H, s)

Example 9

N-[(5-Bromo-1,3-thiazol-2-yl)carbamoyl]-4-(2-chlorophenoxy)benzenesulfonamide

The title compound, MS: m/e 486.0 (MH$^-$), was prepared analogously to the procedure described for Example 2, using 4-(2-chloro-phenoxy)-benzenesulfonyl chloride.

Example 10

N-[(5-Bromo-1,3-thiazol-2-yl)carbamoyl]-3,5-dimethylbenzenesulfonamide

The title compound, MS: m/e 388.0 (MH$^-$), was prepared analogously to the procedure described for Example 2, using 3,5-dimethyl-benzenesulfonyl chloride.

Example 11

N-[(5-Bromo-1,3-thiazol-2-yl)carbamoyl]-4-[(3,4-dichloro-1-methyl-1H-pyrazol-5-yl)oxy]benzenesulfonamide i) diphenyl (5-bromo-1,3-thiazol-2-yl)imidodicarbonate Phenyl chloroformate (1.4 ml, 11.0 mmol) was slowly added to a suspension of 5-bromo-thiazol-2-ylamine hydrobromide (1.3 g, 5.0 mmol) in 20 ml pyridine under an argon atmosphere. The reaction mixture was stirred for 3 h at room temperature and then concentrated under reduced pressure. The residue was suspended in water and acidified using conc. HCl to yield light brown crystals (2.3 g, 93%), m/e 419.2 (MH$^+$).

ii) N-[(5-bromo-1,3-thiazol-2-yl)carbamoyl]-4-[(3,4-dichloro-1-methyl-1H-pyrazol-5-yl)oxy]benzenesulfonamide 4-(4,5-dichloro-2-methyl-2H-pyrazol-3-yloxy)-benzenesulfonamide (77.3 mg, 0.24 mmol) and diphenyl (5-bromo-1,3-thiazol-2-yl)imidodicarbonate (100 mg, 0.24 mmol) were suspended in DMF (0.4 ml). A solution of DBU (0.04 ml, 0.26 mmol) in DMF (0.1 ml) was added dropwise and the clear mixture was shaken for 1.5 h at rt and kept overnight at 4° C. The mixture was acidified using acetic acid (0.2 ml) and diluted with water (0.2 ml) and purified directly using preparative RP($C_{18}$)chromatography: lyophilisate 9 mg, MS: m/e 523.8 (MH$^-$).

Example 12

N-[(5-Bromo-1,3-thiazol-2-yl)carbamoyl]-4-(2-methyl-1,3-thiazol-4-yl)benzenesulfonamide The title compound, MS: m/e 457.1 (MH$^-$), was prepared analogously to the procedure described for Example 2, using 4-(2-methyl-thiazol-4-yl)-benzenesulfonyl chloride.

Example 13

N-[(5-Bromo-1,3-thiazol-2-yl)carbamoyl]-5-methylthiophene-2-sulfonamide

The title compound, MS: m/e 380.0 (MH$^+$), was prepared analogously to the procedure described for Example 2, using 5-methyl-thiophene-2-sulfonyl chloride.

Example 14

N-[(5-Bromo-1,3-thiazol-2-yl)carbamoyl]-5-phenylthiophene-2-sulfonamide

The title compound, MS: m/e 445.7 (MH$^+$), was prepared analogously to the procedure described for Example 2, using 5-phenyl-thiophene-2-sulfonyl chloride.

Example 15

N-[(5-Bromo-1,3-thiazol-2-yl)carbamoyl]biphenyl-4-sulfonamide

The title compound, MS: m/e 436.0 (MH$^-$), was prepared analogously to the procedure described for Example 2, using biphenyl-4-sulfonyl chloride.

Example 16

N-[(5-Bromo-1,3-thiazol-2-yl)carbamoyl]-5-chlorothiophene-2-sulfonamide

The title compound, MS: m/e 399.9 (MH$^-$), was prepared analogously to the procedure described for Example 2, using 5-chloro-thiophene-2-sulfonyl chloride.

Example 17

N-[(5-Bromo-1,3-thiazol-2-yl)carbamoyl]-3-fluorobenzenesulfonamide

The title compound, MS: m/e 378.0 (MH$^-$), was prepared analogously to the procedure described for Example 2, using 3-fluoro-benzenesulfonyl chloride.

Example 18

N-[(5-Bromo-1,3-thiazol-2-yl)carbamoyl]-3-methoxybenzenesulfonamide

The title compound, MS: m/e 389.9 (MH$^-$), was prepared analogously to the procedure described for Example 2, using 3-methoxy-benzenesulfonyl chloride.

Example 19

N-[(5-Bromo-1,3-thiazol-2-yl)carbamoyl]-2,5-dichlorothiophene-3-sulfonamide

The title compound, MS: m/e 437.6 (MH$^+$), was prepared analogously to the procedure described for Example 2, using 2,5-dichloro-thiophene-3-sulfonyl chloride.

Example 20

N-[(5-Bromo-1,3-thiazol-2-yl)carbamoyl]-3,4-difluorobenzenesulfonamide

The title compound, MS: m/e 395.9 (MH$^-$), was prepared analogously to the procedure described for Example 2, using 3,4-difluoro-benzenesulfonyl chloride.

Example 21

N-[(5-Bromo-1,3-thiazol-2-yl)carbamoyl]-4-methoxybenzenesulfonamide

The title compound, MS: m/e 389.9 (MH$^-$), was prepared analogously to the procedure described for Example 2, using 4-methoxy-benzenesulfonyl chloride.

Example 22

N-[(5-Bromo-1,3-thiazol-2-yl)carbamoyl]-4-chlorobenzenesulfonamide

The title compound, MS: m/e 394.0 (MH$^-$), was prepared analogously to the procedure described for Example 2, using 4-chloro-benzenesulfonyl chloride.

Example 23

N-[(5-Bromo-1,3-thiazol-2-yl)carbamoyl]-4-(4-cyclohexyl-2-methyl-1,3-oxazol-5-yl)-2-fluorobenzenesulfonamide The title compound, MS: m/e 541.0 (MH$^-$), was prepared analogously to the procedure described for Example II, using 4-(4-cyclohexyl-2-methyl-oxazol-5-yl)-2-fluoro-benzenesulfonamide.

Example 24

N-[(5-Bromo-1,3-thiazol-2-yl)carbamoyl]-4-(2-methoxyphenoxy)benzenesulfonamide

The title compound, MS: m/e 482.1 (MH$^-$), was prepared analogously to the procedure described for Example 2, using 4-(2-methoxy-phenoxy)-benzenesulfonyl chloride.

Example 25

N-[(5-Bromo-1,3-thiazol-2-yl)carbamoyl]-3-nitrobenzenesulfonamide

The title compound, MS: m/e 405 (MH$^+$), was prepared analogously to the procedure described for Example 2, using 3-nitro-benzenesulfonyl chloride.

Example 26

N-[(5-Bromo-1,3-thiazol-2-yl)carbamoyl]-4-(1,3-oxazol-5-yl)benzenesulfonamide The title compound, MS: m/e 429.1 (MH$^-$), was prepared analogously to the procedure described for Example 2, using 4-oxazol-5-yl-benzenesulfonyl chloride.

Example 27

N-[(5-Bromo-1,3-thiazol-2-yl)carbamoyl]-3,5-difluorobenzenesulfonamide

The title compound, MS: m/e 395.9 (MH$^+$), was prepared analogously to the procedure described for Example 2, using 3,5-difluoro-benzenesulfonyl chloride.

Example 28

N-[(5-Bromo-1,3-thiazol-2-yl)carbamoyl]-4-fluorobenzenesulfonamide

The title compound, MS: m/e 378.0 (MH$^-$), was prepared analogously to the procedure described for Example 2, using 4-fluoro-benzenesulfonyl chloride.

Example 29

N-[(5-Bromo-1,3-thiazol-2-yl)carbamoyl]-4-methyl-benzenesulfonamide

A solution of toluene-4-sulfonylurea isocyanate (2.6 g, 13 mmol) in CH$_2$Cl$_2$ (10 ml) was added slowly to a mixture containing 2-amino-5-bromothiazole hydrochloride (3.4 g, 13 mmol) and triethylamine (5.4 ml, 39 mmol) in CH$_2$Cl$_2$ (60 ml) under an argon atmosphere and stirred overnight at rt. The reaction mixture was concentrated under reduce pressure, diluted with ethyl acetate and washed with NaHCO$_3$ (half sat. 3×), 5% KHSO$_4$/10% K$_2$SO$_4$, water, NaCl sat., dried (MgSO$_4$.2H$_2$O), filtered and concentrated under reduced pressure. Recrystallization from MeOH/water yielded a beige solid: 2.8 g (58%), MS: m/e 376.1 (MH$^+$).

Example 30

N-[(5-Bromo-1,3-thiazol-2-yl)carbamoyl]-4-ethyl-benzenesulfonamide

The title compound, MS: m/e 390.1 (MH$^-$), was prepared analogously to the procedure described for Example 2, using 4-ethyl-benzenesulfonyl chloride.

Example 31

N-[(5-Bromo-1,3-thiazol-2-yl)carbamoyl]benzenesulfonamide

The title compound, MS: m/e 359.9 (MH$^-$), was prepared analogously to the procedure described for Example 2, using benzenesulfonyl chloride.

Example 32

N-[(5-Bromo-1,3-thiazol-2-yl)carbamoyl]-4-(1,2,3-thiadiazol-4-yl)benzenesulfonamide The title compound, MS: m/e 443.9 (MH$^-$), was prepared analogously to the procedure described for Example 2, using 4-[1, 2, 3]thiadiazol-4-yl-benzenesulfonyl chloride.

Example 33

N-[(5-Bromo-1,3-thiazol-2-yl)carbamoyl]-3-(trifluoromethoxy)benzenesulfonamide The title compound, MS: m/e 444 (MH$^+$), was prepared analogously to the procedure described for Example 2, using 4-trifluoromethoxy-benzenesulfonyl chloride.

Example 34

N-[(5-{[(5-Tert-butyl-1,3-oxazol-2-yl)methyl]thio}-1,3-thiazol-2-yl)carbamoyl]-3-methylbenzenesulfonamide The title compound, MS: m/e 467 (MH$^+$), was prepared analogously to the procedure described for Example 39, using 5-(5-tert-butyl-oxazol-2-ylmethylsulfanyl)-thiazol-2-ylamine.

Example 35

3-Methyl-N-{[5-(2-thienyl)-1,3-thiazol-2-yl]carbamoyl}benzenesulfonamide

The title compound, MS: m/e 378.1 (MH$^-$), was prepared analogously to the procedure described for Example 39, using 5-thiophen-2-yl-thiazol-2-ylamine.

Example 36

N-[(4-Chloro-1,3-thiazol-2-yl)carbamoyl]-3-methylbenzenesulfonamide

The title compound, MS: m/e 332 (MH$^+$), was prepared analogously to the procedure described for Example 39, using 4-chloro-thiazol-2-ylamine.

Example 37

N-{[5-(Benzylthio)-1,3-thiazol-2-yl]carbamoyl}-3-methylbenzenesulfonamide

The title compound, MS: m/e 420 (MH$^+$), was prepared analogously to the procedure described for Example 39, using 5-benzylsulfanyl-thiazol-2-ylamine.

Example 38

N-(1,3-Benzothiazol-2-ylcarbamoyl)-3-methylbenzenesulfonamide

The title compound, MS: m/e 348 (MH+), was prepared analogously to the procedure described for Example 39, using benzothiazol-2-ylamine.

Example 39

N-[(4,5-Dimethyl-1,3-thiazol-2-yl)carbamoyl]-3-methylbenzenesulfonamide m-Toluenesulfonyl chloride (0.076 ml, 0.53 mmol, 1.4 equiv.) and pyridine (0.103 ml, 1.27 mmol, 3.4 equiv.) were added to a stirred suspension of sodium cyanate (56 mg, 0.86 mmol, 2.3 equiv.) in dry acetonitrile (1 ml) and the mixture stirred at room temperature for 3 hours. 2-Amino-4,5-dimethylthiazole hydrochloride (34 mg, 0.28 mmol, 1.0 equiv.) was added and the reaction stirred for 1 hour. Water (2 ml) and acetic acid (3 drops) were added. The resulting precipitate was centrifuged for 10 minutes and the supernatant decanted. The solid washed with water (2 ml), the material centrifuged and supernatant decanted. The solid was dried under reduced pressure at 40° C. to give N-[(4,5-dimethyl-1,3-thiazol-2-yl)carbamoyl]-3-methylbenzenesulfonamide, 49 mg (55% yield). LC @UV215 nm; Rt 1.81: 93%, m/z (ES+): 326 (MH+), 651 (2 MH+); $\delta_H$(400 MHz; d4-methanol) 7.54-7.98 (4H, m), 2.57 (3H, s), 2.31 (3H, s), 2.27 (3H, s).

Example 40

N-[(5-Bromo-1,3-thiazol-2-yl)carbamoyl]-2-ethyl-2'-methylbiphenyl-4-sulfonamide, monosodium salt The title compound, MS: m/e 478.0 (MH−), was prepared analogously to the procedure described for Example 43, using 4-bromo-2-ethyl-1-iodo-benzene and 1-bromo-2-methylbenzene in the first step. The sodium salt was prepared as a lyophilisate by dissolving the free acid in acetonitrile and adjusting the pH to 7.2 using 0.01 M NaOH and freeze-drying.

Example 41

N-[(5-Bromo-1,3-thiazol-2-yl)carbamoyl]-2-ethylbiphenyl-4-sulfonamide

The title compound, MS: m/e 464.1 (MH−), was prepared analogously to the procedure described for Example 43, using 4-bromo-2-ethyl-1-iodo-benzene and bromobenzene in the first step.

Example 42

N-[(5-Bromo-1,3-thiazol-2-yl)carbamoyl]-2-ethyl-3'-methylbiphenyl-4-sulfonamide, monosodium salt The title compound, MS: m/e 480.2 (MH−), was prepared analogously to the procedure described for Example 43, using 4-bromo-2-ethyl-1-iodo-benzene and 1-bromo-3-methylbenzene in the first step.

Example 43

N-[(5-Bromo-1,3-thiazol-2-yl)carbamoyl]-2,6-dimethylbiphenyl-4-sulfonamide i) Preparation of 4-bromo-2,6-dimethylbiphenyl 2.5 M n-Butyllithium, in tetrahydrofuran, (1.42 ml, 3.54 mmol, 1.1 equiv.) was added dropwise to a solution of bromobenzene (0.34 ml, 3.22 mmol, 1.0 equiv.) in dry tetrahydrofuran (18 ml), under nitrogen at −78° C. and the mixture stirred for 30 minutes. Zinc chloride (0.48 g, 3.54 mmol, 1.1 equiv.) was added and the mixture allowed to warm to room temperature while stirring for 2 hours. Palladium tetrakistriphenylphosphine (0.19 g, 0.16 mmol, 0.05 equiv.) and a solution of 5-bromo-2-iodo-1,3-dimethyl-benzene (1.00 g, 3.22 mmol, 1.0 equiv.) in tetrahydrofuran (2 ml) were added and the mixture stirred at room temperature for 16 hours. The tetrahydrofuran was evaporated under reduced pressure and the crude product purified by column chromatography ($SiO_2$, heptane). The fractions were combined to afford 4-bromo-2,6-dimethylbiphenyl, 278 mg (33% yield) as a clear oil $\delta_H$ (400 MHz; d4-methanol) 7.28-7.39 (3H, m), 7.18 (2H, s), 7.03 (2H, d), 1.90 (6H, s).

ii) Preparation of 2,6-dimethylbiphenyl-4-sulfonyl chloride 2.5 M n-butyllithium, in tetrahydrofuran, (0.46 ml, 1.17 mmol, 1.1 equiv.) was added dropwise to a solution of 4-bromo-2,6-dimethylbiphenyl (0.28 g, 1.06 mmol, 1.0 equiv.) in dry tetrahydrofuran (5 ml), under nitrogen at −78° C. and the mixture stirred for 15 minutes. This solution was added, by canula, to a solution of sulfur dioxide (3 mL) and tetrahydrofuran (3 ml) under nitrogen at −78° C. The solution was allowed to warm to room temperature while stirring for 16 hours. The solvent was evaporated under reduced pressure and the residue suspended in hexane (4 ml) and dichloromethane (4 ml). The suspension was cooled to 0° C., a solution of sulfuryl chloride (0.14 g, 1.06 mmol, 1.0 equiv.) in hexane (2 ml) was added and the mixture was allowed to warm to room temperature while stirring for 1.5 hours. The hexane and dichloromethane were evaporated under reduced pressure to afford crude 2,6-dimethylbiphenyl-4-sulfonyl chloride, 0.22 g (74% yield) as a red gum, this material was used in the next step without further purification.

iii) Preparation of N-[(5-Bromo-1,3-thiazol-2-yl)carbamoyl]-2,6-dimethylbiphenyl-4-sulfonamide 2,6-Dimethylbiphenyl-4-sulfonyl chloride (0.147 g, 0.53 mmol, 1.4 equiv.) and pyridine (0.152 ml, 1.87 mmol, 5.0 equiv.) were added to a stirred suspension of sodium cyanate (56 mg, 0.86 mmol, 2.3 equiv.) in dry acetonitrile (1.5 ml) and the mixture stirred at room temperature for 3 hours. 5-Bromothiazol-2-ylamine hydrobromide (97 mg, 0.38 mmol, 1.0 equiv.) was added and the reaction stirred for 1 hour. Water (2 ml) and acetic acid (3 drops) were added. The product was extracted into dichloromethane (2 ml), dried over sodium sulfate and evaporated to a brown gum. The gum was purified by preparative HPLC to give N-[(5-bromo-1,3-thiazol-2-yl)

carbamoyl]-2,6-dimethylbiphenyl-4-sulfonamide, 15 mg (9% yield). LC @UV215 nm; Rt 2.64: 96%, m/z (ES+): 467, 468 (M+H).

Example 44

N-[(5-Bromo-1,3-thiazol-2-yl)carbamoyl]-4-(4-methyl-1,3-oxazol-5-yl)benzenesulfonamide i) 4-Methyl-5-phenyl-oxazole To a solution of 1-methyl-1-tosylmethyl isocyamide (2.1 g, 10 mmol) in ethanol (20 ml) were added benzaldehyde (1.0 ml, 10 mmol) and potassium carbonate (2.1 g, 15 mmol). The reaction mixture was refluxed for 5 h under argon. The reaction mixture was concentrated and the residue extracted in ethyl acetate and washed with water, 1 N HCl (3×), NaHCO$_3$ (½ sat., 3×) NaCl sat., dried (MgSO$_4$.2H$_2$O), filtered and solvent was removed under reduced pressure. The crude brown oil was purified over silica gel (ethyl acetane/n-heptane 1:5 to 1:3): crystalline solid, 0.75 g (45%), MS: m/e 160.2 (MH$^+$).

ii) 4-(4-Methyl-oxazol-5-yl)-benzenesulfonyl chloride

To a chilled solution (ice-bath) of 4-methyl-5-phenyl-oxazole (0.2 g, 1.3 mmol) in CHCl$_3$ (1 ml) was added drop-wise chlorosulfonic acid (0.5 ml, 7.7 mmol). The dark-brown reaction mixture was stirred at 4° C. for 30 min and slowly warmed to reflux. After 2 h the reaction mixture was poured into ice-water and extracted with ethyl acetate (3×). The combined organic extracts were washed with water, brine, dried (MgSO$_4$.2H$_2$O), filtered and evaporated to yield a light-brown solid: 0.19 g, (56%), MS: m/e 257.1.

iii) N-[(5-bromo-1,3-thiazol-2-yl)carbamoyl]-4-(4-methyl-1,3-oxazol-5-yl)benzenesulfonamide The title compound, MS: m/e 443.1 (MH$^-$), was prepared analogously to the procedure described for Example 2, using 4-(4-methyl-oxazol-5-yl)-benzenesulfonyl chloride.

Example 45

N-[(5-Bromo-1,3-thiazol-2-yl)carbamoyl]-5-chloro-6-(2-methylpyrrolidin-1-yl)pyridine-3-sulfonamide i) N-[(5-Bromo-1,3-thiazol-2-yl)carbamoyl]-5,6-dichloropyridine-3-sulfonamide The title compound, MS: m/e 529.0 (MH$^-$), was prepared analogously to the procedure described for Example 2, using 2,3-dichloropyridine-5-sulfonyl chloride.

ii) N-[(5-Bromo-1,3-thiazol-2-yl)carbamoyl]-5-chloro-6-(2-methylpyrrolidin-1-yl)pyridine-3-sulfonamide N-[(5-Bromo-1,3-thiazol-2-yl)carbamoyl]-5,6-dichloropyridine-3-sulfonamide (20 mg, 0.05 mmol) was dissolved in DMF (1 ml) and reacted with 2-methylpyrrolidine (0.10 ml, 1 mmol) at 50° C. for 2.5 hours. The reaction mixture was diluted with ethyl acetate (30 ml) and washed with water, NaHCO$_3$ (half sat. 3×), 5% KHSO$_4$/10% K$_2$SO$_4$, NaCl sat., dried (MgSO$_4$.2H$_2$O), filtered and concentrated under reduced pressure. The crude was purified by preparative RP-HPLC: 6 mg, MS: m/e 477.9 (MH$^-$).

Example 46

N-[(5-Bromo-1,3-thiazol-2-yl)carbamoyl]-5-chloro-6-[(2S)-2-(methoxymethyl)pyrrolidin-1-yl]pyridine-3-sulfonamide The title compound, MS: m/e 508.0 (MH$^-$), was prepared analogously to the procedure described for Example 45, using (S)-2-(methoxymethyl)pyrrolidine in step 2.

Example 47

N-[(5-Bromo-1,3-thiazol-2-yl)carbamoyl]-5-chloro-6-(2-isopropylpyrrolidin-1-yl)pyridine-3-sulfonamide The title compound, MS: m/e 506.0 (MH$^-$), was prepared analogously to the procedure described for Example 45, using 2-(methylethyl)pyrrolidine in step 2.

Example 48

N-[(5-Bromo-1,3-thiazol-2-yl)carbamoyl]-3-ethyl-benzenesulfonamide i) 3-Ethyl-benzenesulfonyl chloride 3-Ethyl-phenylamine (2.4 g, 20 mmol) was added drop-wise to a stirred mixture containing HCl conc. (37%, 12 ml) and acetic acid (5 ml) at 5° C. (ice-salt bath). A solution of sodium nitrite (1.5 g, 22 mmol) in water (3 ml) was added dropwise at 0° C. and the resultant black slurry was further stirred at the low temperature for 30 min. A copper (I) chloride (0.5 g, 5 mmol) solution in acetic acid (50 ml) was saturated with SO$_2$ gas. To this saturated solution was added the above, black slurry at 0-5° C. and the reaction was allowed to warm to room temperature and further stirred for 45 min. Ice-water (300 ml) was added the resultant mixture was extracted with ethyl acetate (3×) and the combined organic extracts were washed with water, brine, dried (MgSO$_4$.2H$_2$O) filtered and concentrated under reduced pressure. The crude black oil was purified over silica gel (diethyl ether/n-heptane 1:10): yellow oil, 0.68 g (14%), MS: m/e 204.2 (MH$^+$).

ii) N-[(5-Bromo-1,3-thiazol-2-yl)carbamoyl]-3-ethylbenzenesulfonamide

The title compound, MS: m/e 388.0 (MH$^-$), was prepared analogously to the procedure described for Example 2, using 3-ethyl-benzenesulfonyl chloride.

Example 49

N-[(5-Bromo-1,3-thiazol-2-yl)carbamoyl]-3-isopropylbenzenesulfonamide

The title compound, MS: m/e 402.2 (MH$^-$), was prepared analogously to the procedure described for Example 48, using 3-isopropyl-phenylamine in the first step.

Example 50

N-[(5-Bromo-1,3-thiazol-2-yl)carbamoyl]-5-(4-methoxyphenyl)thiophene-2-sulfonamide i) 5-(4-Methoxy-phenyl)-thiophene-2-sulfonyl chloride

Sulfuryl chloride (0.32 g, 2.34 mmol) was added dropwise a stirred solution of dry DMF (0.18 ml, 2.34 mmol) at 0° C. under an argon atmosphere resulting in the formation of a white solid. After 15 min, 2-(4-methoxy-phenyl)-thiophene (0.38 g, 2 mmol) was added and the mixture was warmed to 100° C. and the melt was further stirred for 45 min. Crushed ice was added and the reaction mixture was extracted with ethyl acetate (2×) and the combined organic extracts were washed with water, brine, dried ($MgSO_4.2H_2O$) filtered and concentrated under reduced pressure. The crude, green solid was purified over silica gel (ethyl acetate/n-heptane 1:9): green solid, 0.13 g (18%).

ii) N-[(5-Bromo-1,3-thiazol-2-yl)carbamoyl]-5-(4-methoxyphenyl)thiophene-2-sulfonamide The title compound, MS: m/e 471.9 ($MH^-$), was prepared analogously to the procedure described for Example 2, using 5-(4-methoxy-phenyl)-thiophene-2-sulfonyl chloride.

Example 51

N-[(5-Bromo-1,3-thiazol-2-yl)carbamoyl]-5-isobutylthiophene-2-sulfonamide i) 2-Methyl-1-thiophen-2-yl-propan-1-one

A mixture containing thiophene (10.1 g, 120 mmol), isobutyric acid (8.8 g, 100 mmol) and 20 g of polyphosphoric acid was magnetically stirred at 75° C. for 2 hours. The reaction mixture was diluted with water (100 ml) and extracted with $CH_2Cl_2$ (2×). The combined organic extracts were washed with water, brine, dried ($Na_2SO_4$), filtered and concentrated under reduced pressure to yield a brown oil: 14 g (77%) GC-MS: M=154.0.

ii) 2-Isobutyl-thiophene

To a mixture of potassium hydroxide (2.24 g, 40 mmol) and hydrazine monohydrate (3.0 g, 60 mmol) in diethylene glycol (25 ml) was added 2-methyl-1-thiophen-2-yl-propan-1-one (1.54 g, 10 mmol). The combined mixture was heated at 180° C. for 1 h and then at 210° C. for a further 2 h. The mixture was cooled to rt and diluted with water (100 ml) and extracted with diethyl ether (3×). The combined organic extracts were washed with water, brine, dried ($Na_2SO_4$) and concentrated under reduced pressure to yield a yellow oil: 0.9 g (61%) GC-MS: M=140.0.

iii) 5-Isobutyl-thiophene-2-sulfonyl chloride

The title compound, GC-MS: M=238.0, was prepared analogously to the procedure described for Example 50 using 2-isobutyl-thiophene in the first step.

iv) N-[(5-Bromo-1,3-thiazol-2-yl)carbamoyl]-5-isobutylthiophene-2-sulfonamide The title compound, MS: m/e 422.0 ($MH^-$), was prepared analogously to the procedure described for Example 2, using 5-isobutyl-thiophene-2-sulfonyl chloride.

Example 52

N-[(5-Bromo-1,3-thiazol-2-yl)carbamoyl]-5-(4-methoxyphenyl)-4-methyl-thiophene-2-sulfonamide i) 2-(4-Methoxy-phenyl)-3-methyl-thiophene

2-Bromo-3-methyl-thiophene (0.53 g, 3.00 mmol) was dissolved in 1,4-dioxane (35 ml) under an argon atmosphere. To this solution were added $Pd(PPh_3)_4$ (0.33 g, 0.28 mmol), 4-methoxyphenyl boronic acid (0.50 g, 3.30 mmol) and 2 M $Na_2CO_3$ (6 ml). The resultant mixture was stirred at 100° C. for 2 hours. The reaction was cooled to rt diluted with tert-.butyl methyl ether and poured into water and extracted with tert.butyl methyl ether (2×). The combined organic extracts were washed with water, brine, dried ($MgSO_4.2H_2O$), filtered and concentrated under reduced pressure to yield a yellow oil that was purified over silica gel (n-heptane) to yield an oil: 0.32 g (48%), GC-MS: M=204.

ii) 5-(4-Methoxy-phenyl)-4-methyl-thiophene-2-sulfonyl chloride

The above sulfonyl chloride, EI-MS: M=304.1, was prepared analogous to Example 50 using 2-(4-methoxy-phenyl)-3-methyl-thiophene in the first step.

ii) N-[(5-Bromo-1,3-thiazol-2-yl)carbamoyl]-5-(4-methoxyphenyl)-4-methyl-thiophene-2-sulfonamide The title compound, MS: m/e 486.2 ($MH^-$), was prepared analogously to the procedure described for Example 2, using 5-(4-methoxy-phenyl)-4-methyl-thiophene-2-sulfonyl chloride.

Example 53

N-[(5-Chloro-1,3-thiazol-2-yl)carbamoyl]-3-methyl-benzenesulfonamide

The title compound, MS: m/e 330.1 ($MH^-$), was prepared analogously to the procedure described for Example 39, using 5-chloro-thiazol-2-ylamine.

Example 54

3-Chloro-N-{[5-(methylthio)-1,3-thiazol-2-yl]carbamoyl}benzenesulfonamide

Sodium methane thiolate (0.42 g, 6.0 mmol) was added to a suspension of N-[(5-bromo-1,3-thiazol-2-yl)carbamoyl]-3-chlorobenzenesulfonamide (0.60 g, 1.5 mmol) in methanol (30 ml). The mixture was heated under refluxed for 60 hours and concentrated under reduced pressure. A part of the crude (80 mg) was dissolved in acetonitrile-water and acidified using acetic acid. The precipitate formed was redissolved in DMSO and purified by preparative RP-HPLC: 14 mg lyophilisate, MS: m/e 362.1 ($MH^-$).

Example 55

N-[(5-Bromo-1,3-thiazol-2-yl)carbamoyl]-3-cyclopropyl-benzenesulfonamide i) 3-Cyclopropyl-benzenesulfonyl chloride Bromo-3-cyclopropyl-benzene (1.0 g, 5.1 mmol) [prep.: J. Org. Chem. vol. 41, 2262-6 (1976)] was dissolved in dry THF/diethyl ether (1:1, 30 ml) under an argon atmosphere and cooled to −78° C. BuLi (1.6 M in hexanes, 3.2 ml, 5.1 mmol) was added dropwise and the reaction mixture was further stirred at low temperature for 15 min. This reaction mixture was added via cannula to a $SO_2$ gas saturated solution of diethyl ether (20 ml) precooled to −78° C. The reaction mixture was stirred overnight at room temperature and concentrated under reduced pressure. The crude intermediate was suspended in n-hexane (4A sieves dried, 20 ml) and chilled (ice-water). A solution of sulfuryl chloride (0.3 ml, 3.6 mmol) in dry hexane (8 ml) was added dropwise to the stirred suspension and then the cold bath was removed. After 90 min at room temperature the reaction mixture was filtered (Speedex pad) and the filtrate was concentrated under reduced pressure to yield a yellow oil: 0.6 g, (67%) GC-MS: M=216.

ii) N-[(5-Bromo-1,3-thiazol-2-yl)carbamoyl]-3-cyclopropyl-benzenesulfonamide

The title compound, MS: m/e 402.3 (MH$^-$), was prepared analogously to the procedure described for Example 2, using 3-cyclopropyl-benzenesulfonyl chloride.

Example 56

N-[(5-Bromo-1,3-thiazol-2-yl)carbamoyl]-2-chlorobenzenesulfonamide

The title compound, MS: m/e 393.9 (MH$^-$), was prepared analogously to the procedure described for Example 2, using 2-chloro-benzenesulfonyl chloride.

Example 57

N-[(5-bromo-1,3-thiazol-2-yl)carbamoyl]-5-(6-methoxypyridin-3-yl)-4-methylthiophene-2-sulfonamide i) 2-Methoxy-5-(3-methyl-thiophen-2-yl)-pyridine The title intermediate, MS: m/e 206.1 (MH$^+$), was prepared analogously to Example 52 from 2-bromo-3-methyl-thiophene and 2-methoxy-5-pyridineboronic acid.

ii) 5-(6-Methoxy-pyridin-3-yl)-4-methyl-thiophene-2-sulfonyl chloride

2-Methoxy-5-(3-methyl-thiophen-2-yl)-pyridine (0.32 g, 1.6 mmol) was dissolved in THF/diethyl ether (10 ml, 1:1 v/v) and cooled to −70° C. BuLi (1.6M hexanes, 1 ml, 1.6 mmol) was added dropwise and after a further 15 min at −70° C. the reaction mixture was added via canula to a condensed solution of $SO_2$ (5 ml) in diethyl ether (10 ml). The yellow colored reaction mixture was slowly warmed to room temperature and stirred overnight. The reaction mixture was concentrated under reduced pressure and the residue washed with diethyl ether and dried. The crude solid (0.31 g) was suspended in dry n-hexane (7 ml), cooled using an ice bath to 0° C. and treated with a solution of sulfuryl chloride (1 M, 1.2 ml, 1.2 mmol) in $CH_2Cl_2$. The reaction mixture was slowly warmed to room temperature and analyzed (TLC) showing no starting material. Solvent was removed under reduced pressure and the crude product was purified over silica gel (n-heptane/tert.butylmethyl ether 1:9 to 1:4 v/v) to yield a white solid: 0.19 g (38%), MS: m/e 304.0 (MH$^+$).

iii) 5-(6-Methoxy-pyridin-3-yl)-4-methyl-thiophene-2-sulfonic acid amide 5-(6-Methoxy-pyridin-3-yl)-4-methyl-thiophene-2-sulfonyl chloride (0.19 g, 0.63 mmol) was dissolved in acetone (6 ml) and added dropwise to an aqueous ammonium hydroxide solution (25%, 1.2 ml). After 1 hour the solvent was removed under reduced pressure, the residue diluted with water and extracted with ethyl acetate (3×). The combined organic extracts were washed with water, brine, dried (MgSO$_4$.2H$_2$O), filtered and concentrated under reduced pressure to yield a crude that was purified over silica gel (n-heptane-ethyl acetate 1:2 to 2:1 v/v) to yield a beige solid: 0.12 g (62%), MS: m/e 283.0 (MH$^-$).

iv) N-[(5-bromo-1,3-thiazol-2-yl)carbamoyl]-5-(6-methoxypyridin-3-yl)-4-methylthiophene-2-sulfonamide

Example 58

N-[(5-bromo-1,3-thiazol-2-yl)carbamoyl]-4-chloro-5-(2-methoxyethyl)thiophene-2-sulfonamide i) 3-Bromo-2-(2-methoxy-ethyl)-thiophene To a solution of 2,3-dibromothiophene (12.6 g, 50 mmol) in THF abs. (125 mL) was added at −75° C. n-BuLi (1.6M/hexane, 31 mL) over 30 minutes. The reaction mixture was further stirred at −75° C. for 30 minutes, and p-toluenesulfonic acid-2-methoxyethylester (11.8 g, 50 mmol) was added dropwise over 1 h. The mixture stirred for 2 h without cooling, quenched with brine, and extracted with ether. The organics were washed, dried, and concentrated. The residue was chromatographed on silica gel using heptane/ethyl acetate as eluent to obtain 3-bromo-2-(2-methoxy-ethyl)-thiophene (1.8 g) as a colorless liquid. MS (EI): 221.1 (M)

ii) 3-Chloro-2-(2-methoxy-ethyl)-thiophene

To a solution of 3-bromo-2-(2-methoxy-ethyl)-thiophene (1.7 g, 8 mmol) in DMF (8 mL) was added copper(I)-chloride (1.42 g, 12 mmol). The reaction mixture was stirred at 140° C. for 18 h, quenched with ice/water, extracted with ether, the organics were washed, dried and concentrated, the residue chromatographed on silica gel using heptane/ethyl acetate as eluent to obtain 3-chloro-2-(2-methoxy-ethyl)-thiophene (1.25 g) as a light brown liquid. MS (EI) m/e 176.1 (M)

iii) 4-Chloro-5-(2-methoxy-ethyl)-thiophene-2-sulfonyl chloride

To a suspension of sulfur trioxide dimethylformamide complex (1.40 g, 9 mmol) in 1,2-dichloroethane (10 mL) was added 3-chloro-2-(2-methoxy-ethyl)-thiophene (Yun, Sangmin; Kim, Eun Sook; Kim, Hee Seock; Ha, Tae Hee; Suh, Kwee-Hyun; Lee, Gwan Sun, WO 2005087779 (1.35 g, 8 mmol). The reaction mixture was stirred at rt for 1 h, thionyl chloride (1.2 g, 10 mmol) was added, and the mixture was stirred at 55-60° C. for 3-4 h and chromatographed directly on silica gel using heptane/ethyl acetate or dichloromethane/ethyl acetate as eluents to obtain 4-chloro-5-(2-methoxy-ethyl)-thiophene-2-sulfonyl chloride (1.6 g) a light yellow liquid.

MS (EI) m/e 274.0 (M)

iv) N-[(5-bromo-1,3-thiazol-2-yl)carbamoyl]-4-chloro-5-(2-methoxyethyl)thiophene-2-sulfonamide The title compound was prepared in analogy to the procedure described for Example 2 starting from 4-chloro-5-(2-methoxy-ethyl)-thiophene-2-sulfonyl chloride to obtain the desired compound as a brownish solid. MS (ISN): m/e 458.0, 459.9, (M–H)$^+$

Example 59

N-[(5-Bromo-1,3-thiazol-2-yl)carbamoyl]-5-(4-methoxy-2-methylphenyl)-4-methylthiophene-2-sulfonamide i) 2-(4-Methoxy-2-methyl-phenyl)-3-methyl-thiophene

The compound was prepared analogously to the procedure described for example 521) using 4-methoxy-2-methyl-phenyl boronic acid to give 2-(4-methoxy-2-methyl-phenyl)-3-methyl-thiophene, 910 mg, m/e 218.2 (MH$^+$).

ii) 5-(4-Methoxy-2-methyl-phenyl)-4-methyl-thiophene-2-sulfonyl chloride

The compound was prepared analogously to the procedure described for example 501) using 2-(4-methoxy-2-methyl-phenyl)-3-methyl-thiophene to give 5-(4-methoxy-2-methyl-phenyl)-4-methyl-thiophene-2-sulfonyl chloride as a light yellow oil, 350 mg, m/e 316.1 (MH$^+$).

iii) N-[(5-bromo-1,3-thiazol-2-yl)carbamoyl]-5-(4-methoxy-2-methylphenyl)-methylthiophene-2-sulfonamide 5-(4-Methoxy-2-methyl-phenyl)-4-methyl-thiophene-2-sulfonyl chloride (95 mg, 0.30 mmol, 1.5 equiv.) was dissolved in 0.3 ml MeCN, followed by the addition of sodium cyanate (28.6 mg, 0.44 mmol, 2.2 equiv.). Under strong stirring, pyridine (0.055 ml, 0.68 mmol, 3.4 equiv.) was added dropwise to the reaction mixture which was further stirred for 4 hrs at rt. 2-Amino-5-bromothiazole. HBr (52 mg, 0.20 mmol, 1.0 equiv.), was added and the reaction stirred for 1 hour. Water (20 ml) and 70% acetic acid (2 ml) were added to the suspension which was filtered, washed with water and cold MeOH. The crude solid was dissolved in MeCN-DMSO and chromatographed on a HPLC 75×30 mm RP 18 5 µm column, with A=0.1% HCOOH and B=MeCN and with a gradient of 40% to 90% B in 10 min. The desired fractions were lyophilized to give N-[(5-bromo-1,3-thiazol-2-yl)carbamoyl]-5-(4-methoxy-2-methylphenyl)-4-methylthiophene-2-sulfonamide, 16 mg, m/e 499.9 (MH$^-$).

Example 60

N-[(5-Bromo-1,3-thiazol-2-yl)carbamoyl]-4-(6-methoxypyridin-3-yl)-3-methylbenzenesulfonamide i) N-tert-Butyl-4-(6-methoxy-pyridin-3-yl)-3-methyl-benzenesulfonamide

This compound was prepared analogous to Example 64, starting with 4-bromo-n-tert-butyl-3-methyl-benze (1 g, 3.26 mmol) and 2-methoxy-5-pyridineboronic acid (550 mg, 3.6 mmol, 1.1 equiv.) to obtain 995 mg of the title compound as a colorless gum. MS (ES): m/e 333.3 (M–H)

ii) 4-(6-Methoxy-pyridin-3-yl)-3-methyl-benzene-sulfonamide

This compound was prepared analogous to Example 64 starting with n-tert-butyl-4-(6-methoxy-pyridin-3-yl)-3-methyl-benzenesulfonamide (930 mg, 2.78 mmol) to obtain 750 mg of the title compound as a white solid. MS (ES): m/e 277.3 (M–H)

iii) N-[(5-Bromo-1,3-thiazol-2-yl)carbamoyl]-4-(6-methoxypyridin-3-yl)-3-methylbenzenesulfonamide This compound was prepared analogous to Example 64, starting with 4-(6-methoxy-pyridin-3-yl)-3-methyl-benzene-sulfonamide (200 mg, 0.72 mmol) to obtain 33 mg of the title compound as a light brown, amorphous solid. MS (ES): m/e 481.2 (M–H)

Example 61

N-[(5-Bromo-1,3-thiazol-2-yl)carbamoyl]-5-isobutyl-4-methylthiophene-2-sulfonamide i) 2-Isobutyl-3-methyl-thiophene

A part of a solution containing 2-bromo-3-methylthiophene (1.5 g, 8.5 mmol) in dry diethyl ether is added dropwise to a suspension of magnesium (308 mg, 12.7 mmol, 1.5 equiv.) in dry diethyl ether until the mixture starts to reflux. The remaining solution is added dropwise. A solution of toluene-4-sulfonic acid isobutyl ester (2.9 g, 12.7 mmol, 1.5 equiv.) in dry diethyl ether is added dropwise at room temp., then the mixture is further refluxed for two hours. After cooling to room temp., the mixture is quenched with sat. ammonium chloride solution and extracted with tert. butylmethyl-ether. The combined organic extracts are washed with water, brine, dried over magnesiumsulfat-dihydrate, filtered and evaporated to give a yellow oil. After Kugelrohr-distillation, 630 mg of the title compound is obtained as a colorless oil. GC-MS (EI): M=154 ii) 5-Isobutyl-4-methyl-thiophene-2-sulfonyl chloride 190 mg of the title compound, GC-MS: M=252, was prepared analogously to the procedure described for Example 50 starting from 2-isobutyl-3-methyl-thiophene (350 mg, 1.93 mmol).

iii) N-[(5-Bromo-1,3-thiazol-2-yl)carbamoyl]-5-isobutyl-4-methylthiophene-2-sulfonamide This compound is prepared analogous to Example 2 starting with 5-isobutyl-4-methyl-thiophene-2-sulfonyl chloride (187 mg, 0.74 mmol) and 5-bromo-thiazol-2-ylamine hydrobromide (140 mg, 0.54 mmol, 0.73 equiv.). After purification on preparative HPLC, 49 mg of the title compound was obtained as a white, amorphous solid. MS (ES): m/e 436.1 (M−H)

Example 62

3-methyl-N-({4-methyl-5-[(trifluoromethyl)thio]-1,3-thiazol-2-yl}carbamoyl)benzenesulfonamide This compound was prepared analogous to Example 2, starting with 3-methyl-benzenesulfonyl chloride (122 mg, 0.64 mmol) and 4-methyl-5-trifluoromethylsulfanyl-thiazol-2-ylamine (100 mg, 0.466 mmol, 0.73 equiv.). After purification on preparative HPLC, 46 mg of the title compound is obtained as a white, amorphous solid. MS (ES): m/e 410.0 (M−H)

Example 63

N-[(5-Bromo-1,3-thiazol-2-yl)carbamoyl]-5-(2-methoxyethyl)-4-methylthiophene-2-sulfonamide i) 2-(2-Methoxy-ethyl)-3-methyl-thiophene

This compound was prepared analogous to Example 61, starting with 2-bromo-3-methylthiophene (1.5 g, 8.5 mmol) and toluene-4-sulfonic acid 2-methoxy-ethyl ester (2.9 g, 12.7 mmol, 1.5 equiv.) The crude product was purified on silica gel with eluent n-heptane and tert.butylmethyl ether. The title compound was obtained as a light yellow oil, 490 mg. GC-MS (EI): M=156 ii) 5-(2-Methoxy-ethyl)-4-methyl-thiophene-2-sulfonyl chloride

This compound was prepared analogous to Example 61, starting with 2-(2-methoxy-ethyl)-3-methyl-thiophene. (250 mg, 1.6 mmol). The title compound was obtained as a light yellow oil 220 mg. GC-MS (EI): M=254.

iii) N-[(5-Bromo-1,3-thiazol-2-yl)carbamoyl]-5-(2-methoxyethyl)-4-methylthiophene-2-sulfonamide This compound was prepared analogous to Example 2, starting with 5-(2-methoxy-ethyl)-4-methyl-thiophene-2-sulfonyl chloride (210 mg, 0.742 mmol) and 5-bromo-thiazol-2-ylamine hydrobromide (141 mg, 0.542 mmol, 0.73 equiv.). After purification on preparative HPLC, the title compound was obtained as a white, amorph, freeze-dried solid: 38 mg. MS (ES): m/e 438.0 (M−H)

Example 64

N-[(5-Bromo-1,3-thiazol-2-yl)carbamoyl]-4-(6-fluoropyridin-3-yl)-3-methylbenzenesulfonamide i) 4-Bromo-N-tert-butyl-3-methyl-benzenesulfonamide

To a stirred, ice-cold solution of 4-bromo-3-methyl-benzenesulfonyl chloride (11 g, 40.8 mmol) and N'N-diisopropyl-ethylamine (8.5 ml, 49 mmol, 1.2 equiv.) in dichloromethane was added dropwise tert. butylamine (5.2 ml, 49 mmol, 1.2 equiv.). After two hours at room temp., the reaction mixture was diluted with water and extracted with dichloromethane. The organic extracts were concentrated under reduced pressure, the residue stirred with n-heptane and filtered to obtain 11.2 g of the desired compound as a yellow solid. MS (ES): m/e 304.2 (M−H)

ii) N-tert-Butyl-4-(6-fluoro-pyridin-3-yl)-3-methyl-benzenesulfonamide

This compound was prepared analogous to Example 52 starting from 4-bromo-n-tert-butyl-3-methyl-benzenesulfonamide (11 g, 36.2 mmol) to obtain 10.8 g of the desired compound as a light yellow gum. MS (ES): m/e 321.3 (M−H)

iii) 4-(6-Fluoro-pyridin-3-yl)-3-methyl-benzenesulfonamide n-tert-Butyl-4-(6-fluoro-pyridin-3-yl)-3-methyl-benzenesulfonamide (10.4 g, 32.4 mmol) was treated with a mixture of 225 ml trifluoroacetic acid and 25 ml water, for 2 hours at 50° C. The mixture was concentrated and the residue dissolved in ethyl acetate and extracted with an aqueous sodium bicarbonate solution. The combined organic extracts were washed with brine, dried over magnesiumsulfat-dihydrate, filtered and evaporated to give 7.3 g of the title compound as a light yellow solid. MS (ES): m/e 264.9 (M−H)

iv) N-[(5-bromo-1,3-thiazol-2-yl)carbamoyl]-4-(6-methoxypyridin-3-yl)-3-methylbenzenesulfonamide To a solution of 4-(6-fluoro-pyridin-3-yl)-3-methyl-benzenesulfonamide (4.2 g, 16 mmol) and triethylamine (5.1 ml, 36.8 mmol, 2.3 equiv.) in 130 ml acetonitrile was added dropwise at 0° C. phenyl chloroformate (2.4 ml, 19.2 mmol, 1.2 equiv.) After stirring the solution for one hour at room temp., 5-bromo-thiazol-2-ylamine (4.3 g, 24 mmol, 1.5 equiv.) is added in one portion. The mixture was warmed to 60° C., then methanesulfonic acid (1.5 ml, 24 mmol, 1.5 equiv.) was added and the reaction mixture was stirred for one hour at 60° C. After cooling to room temp., the mixture was diluted with water and extracted with ethyl acetate. The combined organic extracts were washed with brine, dried over magnesium-dihydrate, filtered and evaporated. The crude product was purified on silica-gel with ethyl acetate/n-heptane to give 2.67 g of the title compound as a light brown solid. MS (ES): m/e 470.7 (M−H)

Example 65

N-[(5-Bromo-1,3-thiazol-2-yl)carbamoyl]-5-(6-fluoropyridin-3-yl)-4-methylthiophene-2-sulfonamide i) 2-Fluoro-5-(3-methyl-thiophen-2-yl)-pyridine

This compound was prepared in analogy to Example 52, starting from 2-bromo-3-methylthiophene (2.6 g, 15 mmol) and 2-fluoro-5-pyridine-boronic acid (2.3 g, 16.5 mmol, 1.1 equiv.) to obtain 2.2 g of the desired compound as a light yellow oil. MS (ES): m/e 194.2 (M+H)

ii) 5-(6-Fluoro-pyridin-3-yl)-4-methyl-thiophene-2-sulfonyl chloride

This compound was prepared in analogy to Example 50 I), starting with 2-fluoro-5-(3-methyl-thiophen-2-yl)-pyridine (1.1 g, 5.7 mmol). 350 mg of the title compound was obtained as a light yellow solid. MS (EI): M=291.1 iii) 5-(6-Fluoro-pyridin-3-yl)-4-methyl-thiophene-2-sulfonic acid amide 5-(6-Fluoro-pyridin-3-yl)-4-methyl-thiophene-2-sulfonyl chloride (310 mg, 1.06 mmol) was dissolved in dioxane and cooled with an ice-bath. Under stirring was added dropwise an excess of ammonium hydroxide solution 25%. After two hours at room temp the reaction was neutralized and the dioxane was evaporated. The reaction mixture was extracted with ethyl acetate, the combined organic extracts were washed with brine, dried over magnesiumsulfat-dihydrate, filtered and evaporated. The crude product was purified on silica-gel with eluent ethyl acetate/n-heptane to give 218 mg of the title compound as a white solid. MS (ES): m/e 271.2 (M−H)

iv) N-[(5-Bromo-1,3-thiazol-2-yl)carbamoyl]-5-(6-fluoropyridin-3-yl)-4-methylthiophene-2-sulfonamide This compound was prepared in analogy to Example 64 iv), starting with 5-(6-fluoro-pyridin-3-yl)-4-methyl-thiophene-2-sulfonic acid amide (200 mg, 0.734 mmol) and 5-bromo-thiazol-2-ylamine hydrobromide (286 mg, 1.1 mmol, 1.5 equiv.). After purification on preparative HPLC, yielding 13 mg of the title compound as a white, amorphous solid. MS (ES): m/e 474.7 (M−H)

Example 66

N-[(5-Bromo-1,3-thiazol-2-yl)carbamoyl]-3-chloro-4-fluorobenzenesulfonamide

This compound was prepared analogously to the procedure described for Example 59 iii), using 3-chloro-4-fluoro-benzenesulfonyl chloride to obtain after crystallization N-[(5-bromo-1,3-thiazol-2-yl)carbamoyl]-3-chloro-4-fluorobenzenesulfonamide, 257 mg, m/e 412.1 (MH−).

Example 67

N-[(5-Bromo-1,3-thiazol-2-yl)carbamoyl]-5-(3-methoxypropyl)-4-methylthiophene-2-sulfonamide i) Toluene-4-sulfonic acid 3-methoxy-propyl ester 4-Methyl-benzenesulfonyl chloride (21 g, 110.0 mmol, 1.1 equiv.) was added at 0° C. to a solution of 3-methoxy-propan-1-ol (9 g, 100.0 mmol, 1.0 equiv.) in pyridine (16.1 ml, 200.0 mmol, 2.0 equiv.). After 1 hr at 0° C. a white solid was formed. It was diluted with water and extracted twice with ethyl acetate. The combined organics were washed with KHSO$_4$/K$_2$SO$_4$ and brine, dried over Na$_2$SO$_4$, filtered, evaporated and crystallized from ether (hygroscopic) to give toluene-4-sulfonic acid 3-methoxy-propyl ester, 21.4 g, m/e 245.0 (MH$^+$).

ii) 2-(3-Methoxy-propyl)-3-methyl-thiophene

Magnesium turnings (365 mg, 15.0 mmol, 1.5 equiv.) were suspended in 15 ml dry diethyl ether. A crystal of iodine and a few drops of 2-bromo-3-methylthiophene in 10 ml ether were added till the reaction started (3 min. with heating to 30° C.). The remaining solution of 2-bromo-3-methylthiophene (total 2.44 g, 10.0 mmol, 1.0 equiv.) was added dropwise to maintain the reaction at reflux. The reaction mixture was refluxed for 30 min. Toluene-4-sulfonic acid 3-methoxy-propyl ester (2.13 g, 12.0 mmol, 1.2 equiv.) dissolved in 5 ml diethyl ether was added dropwise and the yellow solution was refluxed again for 2 hours. The brown suspension was cooled, acidified with 1N HCl and extracted twice with ethyl acetate. The combined organics were washed with KHSO$_4$/K$_2$SO$_4$ and brine, dried over Na$_2$SO$_4$, filtered, evaporated and chromatographed on a 50 g Silicagel cartridge with heptane and than MTBE-heptane 1:9 as solvent to give 2-(3-methoxy-propyl)-3-methyl-thiophene, 410 mg, m/e 170.0 (MH$^+$) by GC/MS.

iii) 5-(3-Methoxy-propyl)-4-methyl-thiophene-2-sulfonyl chloride 2-(3-Methoxy-propyl)-3-methyl-thiophene (409 mg, 2.4 mmol, 1.0 equiv.) dissolved in 1 ml DCE was added drop wise to a suspension of sulfur trioxide dimethylformamide complex (441 mg, 2.88 mmol, 1.2 equiv.) in 2 ml DCE. The reaction mixture was heated to 55° C. for 15 min. and than cooled to rt. Thionyl chloride (0.21 ml, 2.88 mmol, 1.2 equiv.) was added drop wise to the mixture which was than heated to 80° C. for 1 hr. At rt the reaction was treated with ice for 15 min. and than extracted twice with ethyl acetate. The combined organic layers were washed with brine, dried over Na$_2$SO$_4$, filtered, evaporated and chromatographed on a 20 g Silicagel cartridge with ethyl acetate-heptane 1:2 as solvent to give a brown liquid identified as 5-(3-methoxy-propyl)-4-methyl-thiophene-2-sulfonyl chloride, 400 mg, m/e 268.0 (MH$^+$).

iiii) N-[(5-Bromo-1,3-thiazol-2-yl)carbamoyl]-5-(3-methoxypropyl)-4-methylthiophene-2-sulfonamide The compound was prepared analogously to the procedure described for Example 59 iii), using 5-(3-methoxy-propyl)-4-methyl-thiophene-2-sulfonyl chloride to obtain after crystallization N-[(5-bromo-1,3-thiazol-2-yl)carbamoyl]-5-(3-methoxypropyl)-4-methylthiophene-2-sulfonamide, 18 mg, m/e 452.0 (MH$^-$).

Example 68

N-[(5-Bromo-1,3-thiazol-2-yl)carbamoyl]-4-(2-methoxy-1,3-thiazol-4-yl)-3-methylbenzenesulfonamide i) N-tert-Butyl-3-methyl-benzenesulfonamide boronic acid 4-Bromo-N-tert-butyl-3-methyl-benzenesulfonamide (10 g, 32.6 mmol) was dissolved in dry tetrahydrofurane, then cooled to −78° C. Triisopropyl borate (27.7 ml, 120.8 mmol, 3.7 equiv.) was added in one portion, followed by the dropwise addition of n-butyllithium solution 1.6M (75.5 ml, 120.8 mmol, 3.7 equiv.) at −78° C. The mixture was stirred overnight, then quenched dropwise with water. The organic solvent was evaporated and the pH adjusted to 3 with 0.5 M HCl. The residue was extracted with ethyl acetate and the combined organic extracts were washed with brine, dried over magnesiumsulfat-dihydrate, filtered and evaporated. The crude product was purified on silica-gel with ethyl acetate/n- ii) 4-(2-methoxy-4H-1lambda*4*-thiazol-4-yl)-3-methyl-benzenesulfonamide

This compound was prepared analogously to Example 52, starting from N-tert-butyl-3-methyl-benzenesulfonamide boronic acid (1.0 g, 3.69 mmol) and 4-bromo-2-methoxy-thiazole (0.78 g, 4.05 mmol, 1.1 equiv.) After purification on silica-gel with n-heptane/tert.butylmethyl ether 510 mg of the t-butyl protected sulfonamide were obtained. Deprotection analogous to Example 98 yielded 260 mg of the title compound as a light yellow solid. MS (ES): m/e 270 (M−H)

iii) N-[(5-Bromo-1,3-thiazol-2-yl)carbamoyl]-4-(2-methoxy-1,3-thiazol-4-yl)-3-methylbenzenesulfonamide This compound was prepared analogous to Example 64 starting from 4-(2-methoxy-4H-1lambda*4*-thiazol-4-yl)-3-methyl-benzenesulfonamide (180 mg, 0.633 mmol) to obtain 118 mg of the desired compound as a light brown solid. MS (ES): m/e 487.0 (M−H)

Example 69

N-[(5-Bromo-1,3-thiazol-2-yl)carbamoyl]-4-(5-fluoropyridin-3-yl)-3-methylbenzenesulfonamide i) N-tert-Butyl-4-(5-fluoro-pyridin-3-yl)-3-methyl-benzenesulfonamide This compound was prepared analogous to Example 52, starting from N-tert-butyl-3-methyl-benzenesulfonamide boronic acid (0.5 g, 1.84 mmol) and 5-bromo-3-fluoropyridine (357 mg, 2.03 mmol, 1.1 equiv.) After purification on silica-gel with n-heptane/ethyl acetate, 335 mg of the title compound were obtained as a light yellow solid MS (ES): m/e 321.1 (M−H)

ii) N-[(5-Bromo-1,3-thiazol-2-yl)carbamoyl]-4-(5-fluoropyridin-3-yl)-3-methylbenzenesulfonamide This compound was prepared analogous to Example 64, starting from N-tert-butyl-4-(5-fluoro-pyridin-3-yl)-3-methyl-benzenesulfonamide. (174 mg; 0.653 mmol) After purification on silica-gel using ethyl acetate/n-heptane, 107 mg of the title compound were obtained as a light brown solid. MS (ES): m/e 468.9 (M−H)

Example 70

N-[(5-Bromo-1,3-thiazol-2-yl)carbamoyl]-5-methoxy-4-methylthiophene-2-sulfonamide i) 5-methoxy-4-methyl-thiophene-2-sulfonic acid amide 2-methoxy-3-methyl-thiophene (1 g, 7.8 mmol) was dissolved in dry tetrahydrofuran. At −78° C. n-butyllithium 1.6 M in n-hexane (5.1 ml, 8.2 mmol, 1.1 equiv.) were added dropwise. After one hour at −78° C., sulfur dioxide gas was bubbled over the surface of the reaction mixture for 30 min. The reaction mixture was diluted with diethyl ether and allowed to warm to room temp. The solvent was evaporated and the residue is dissolved in dichloromethane. N-chlorosuccinimide (1.1 g, 8.2 mmol, 1.1 equiv.) was added in one portion. After two hours stirring, the mixture is filtered and the filtrate was concentrated under reduced pressure. The residue was dissolved in acetone and an excess of 25% aq. ammonium hydroxide solution was added and the mixture was stirred for 30 min. at room temp. The solvent was evaporated and the remaining oil was dissolved in ethyl acetate and extracted with water, washed with brine, dried over magnesium sulfate dihydrate, filtered and evaporated. After purification on silica-gel with ethyl acetate/n-heptane, 210 mg of the title compound were obtained as a light brown solid. MS (ES): m/e 206.0 (M−H)

ii) N-[(5-bromo-1,3-thiazol-2-yl)carbamoyl]-5-methoxy-4-methylthiophene-2-sulfonamide This compound was prepared analogously to Example 64, starting from 5-methoxy-4-methyl-thiophene-2-sulfonic acid amide (100 mg, 0.482 mmol). After purification on silica-gel using ethyl acetate/n-heptane 53 mg of title compound were obtained as a light brown solid. MS (ES): m/e 409.9 (M−H)

Example 71

N-[(5-Bromo-1,3-thiazol-2-yl)carbamoyl]-5-(2-methoxyethoxy)-4-methylthiophene-2-sulfonamide i) 2-(2-Methoxy-ethoxy)-3-methyl-thiophene 2-methoxy-3-methyl-thiophene, (1.5 g, 11.7 mmol) 2-methoxy-ethanol (3.8 g, 50.5 mmol, 4.3 equiv.) and sodium hydrogen sulfate anhydrous (100 mg, 0.833 mmol, 0.07 equiv.) were stirred in toluene at 120° C. for 3.5 hours. The mixture was diluted with ethyl acetate and extracted with sodium bicarbonate solution. The organic solvent washed with brine, dried over magnesium sulfate dihydrate, filtered and evaporated. After Kugelrohr distillation, 980 mg of the title compound were obtained as a light yellow oil GC-MS (EI) M=172.

ii) 5-(2-Methoxy-ethoxy)-4-methyl-thiophene-2-sulfonic acid amide

This compound was prepared analogous to Example 70, starting from 2-(2-methoxy-ethoxy)-3-methyl-thiophene (910 mg, 5.28 mmol). After purification on silica-gel using ethyl acetate/n-heptane, 180 mg of title compound were obtained as a light brown solid. MS (ES): m/e 250.0 (M−H)

iii) N-[(5-Bromo-1,3-thiazol-2-yl)carbamoyl]-5-(2-methoxyethoxy)-4-methylthiophene-2-sulfonamide This compound was prepared analogous to Example 64, starting from 5-(2-methoxy-ethoxy)-4-methyl-thiophene-2-sulfonic acid amide. (165 mg, 0.657 mmol). After purification on silica-gel with ethyl acetate/n-heptane, 106 mg of the title compound were obtained as a light brown solid. MS (ES): m/e 453.8 (M−H)

Example 72

N-[(5-Bromo-1,3-thiazol-2-yl)carbamoyl]-5-(6-methoxy-4-methylpyridin-3-yl)-4-methylthiophene-2-sulfonamide i) 5-Bromo-2-methoxy-4-methyl-pyridine boronic acid

The title compound, MS: m/e 166.0 (M–H) was prepared analogously to the procedure described for Example 68, using 5-bromo-2-methoxy-4-methyl-pyridine.

ii) 2-Methoxy-4-methyl-5-(3-methyl-thiophen-2-yl)-pyridine

The title compound, MS: m/e 220.3 (M+H) was prepared analogously to the procedure described for Example 52, using 5-bromo-2-methoxy-4-methyl-pyridine boronic acid.

iii) 5-(6-Methoxy-4-methyl-pyridin-3-yl)-4-methyl-thiophene-2-sulfonic acid amide The title compound, MS: m/e 297.2 (M–H) was prepared analogously to the procedure described for Example 70, using 2-methoxy-4-methyl-5-(3-methyl-thiophen-2-yl)-pyridine.

iv) N-[(5-Bromo-1,3-thiazol-2-yl)carbamoyl]-5-(6-methoxy-4-methylpyridin-3-yl)-4-methylthiophene-2-sulfonamide The title compound, MS: m/e 500.8 (M–H) was prepared analogously to the procedure described for Example 64, using 5-(6-methoxy-4-methyl-pyridin-3-yl)-4-methyl-thiophene-2-sulfonic acid amide.

Example 73

N-[(5-Bromo-1,3-thiazol-2-yl)carbamoyl]-5-(methoxymethyl)-4-methylthiophene-2-sulfonamide i) (3-Methyl-thiophen-2-yl)-methanol

Sodium borohydride (6.0 g, 158.5 mmol, 2 equiv.) was suspended in dry tetrahydrofuran under an inert atmosphere. At 10° C. a solution of 3-methyl-thiophene-2-carbaldehyde (10 g, 79.2 mmol, 1 equiv.) in dry tetrahydrofuran was added dropwise. The mixture was stirred at room temp. for 3 hours. The reaction mixture was quenched with diluted acid and filtered. The filtrate was extracted with diethyl ether. The combined organic extracts were washed with brine, dried over magnesium sulfate dihydrate, filtered and evaporated. Kugelrohr distillation of the crude product gave 8.33 g of the title compound as a light yellow oil. GC-MS (EI) M=128 ii) 2-Methoxymethyl-3-methyl-thiophene

Sodium hydride (2.2 g ~60%, 55.2 mmol, 1.2 equiv.) was suspended in dry tetrahydrofuran under an inert atmosphere. At 5° C. a solution of (3-methyl-thiophen-2-yl)-methanol (5.16 g, 46 mmol) in dry tetrahydrofuran was added dropwise. The mixture was stirred at room temp. for 1 hour, then iodomethane (7.8 g, 55.2 mmol, 1.2 equiv.) was added dropwise. The mixture was stirred overnight at room temp. and then quenched with diluted acid and extracted with diethyl ether. The combined organic extracts were washed with brine, dried over magnesiumsulfat dihydrate, filtered and evaporated to give 5.7 g of the title compound as a light green oil. GC-MS (EI) M=142.

iii) 5-Methoxymethyl-4-methyl-thiophene-2-sulfonic acid amide

The title compound, MS: m/e 204.0 (M–H) was prepared analogously to the procedure described for Example 70, using 2-methoxymethyl-3-methyl-thiophene iv) N-[(5-Bromo-1,3-thiazol-2-yl)carbamoyl]-5-(methoxymethyl)-4-methylthiophene-2-sulfonamide The title compound, MS: m/e 423.7 (M–H) was prepared analogously to the procedure described for Example 64, using 5-methoxymethyl-4-methyl-thiophene-2-sulfonic acid amide

Example 74

N-[(5-Bromo-4-methyl-1,3-thiazol-2-yl)carbamoyl]-3-methylbenzenesulfonamide

The title compound, MS: m/e 388.0 (M–H) was prepared analogously to the procedure described for Example 64, using toluene-3-sulfonamide and 5-bromo-4-methyl-thiazol-2-ylamine.

Example 75

N-[(5-Bromo-4-methyl-1,3-thiazol-2-yl)carbamoyl]-3-(difluoromethoxy)benzenesulfonamide

The title compound, MS: m/e 439.9 (M–H) was prepared analogously to the procedure described for Example 2, using 3-difluoromethoxy-benzenesulfonyl chloride and 5-bromo-4-methyl-thiazol-2-ylamine.

Example 76

3-Methyl-N-[(4-methyl-5-nitro-1,3-thiazol-2-yl)carbamoyl]benzenesulfonamide

The title compound, MS: m/e 355.0 (M–H) was prepared analogously to the procedure described for Example 64, using toluene-3-sulfonamide and 4-methyl-5-nitro-thiazol-2-ylamine.

Example 77

N-{[5-Bromo-4-(methoxymethyl)-1,3-thiazol-2-yl]carbamoyl}-3-methylbenzenesulfonamide i) 4-Methoxymethyl-thiazol-2-ylamine 1,3-Dibromoacetone (15 g, 52 mmol) and thiourea (4.05 g, 53.2 mmol, 1.02 equiv.) in methanol were refluxed overnight. The reaction mixture was diluted with water and the pH was adjusted to 1 with HCl 25%, followed by extraction with ethyl acetate. The pH of the aqueous layer was adjusted to 8-9 using solid sodium carbonate. The aqueous layer was extracted with ethyl acetate, and the combined organic extracts were washed with brine, dried over magnesiumsulfat dihydrate, filtered and evaporated. The crude product was purified on silica-gel (NH$_2$-modified) with ethyl acetate/n-heptane as eluent yielding a white solid: 340 mg. MS (ES) m/e 145 (M+H)

ii) 5-Bromo-4-methoxymethyl-thiazol-2-ylamine

4-Methoxymethyl-thiazol-2-ylamine (170 mg, 1.1 mmol) is dissolved in acetonitrile and N-bromosuccinimide. (231 mg, 1.3 mmol, 1.1 equiv.) was added in one portion. The mixture was stirred at room temp. for 2 hours, then filtered and the filtrate was evaporated. After purification on silica-gel with ethyl acetate/n-heptane as eluent, 260 mg of a light red solid were obtained: MS: m/e 222.8 (M+H).

iii) N-{[5-Bromo-4-(methoxymethyl)-1,3-thiazol-2-yl]carbamoyl}-3-methylbenzenesulfonamide The title compound, MS: m/e 417.9 (M–H) was prepared analogously to the procedure described for Example 64, using toluene-3-sulfonamide and 5-bromo-4-methoxymethyl-thiazol-2-ylamine.

Example 78

Ethyl 5-bromo-2-({[(3-methylphenyl)sulfonyl]carbamoyl}amino)-1,3-thiazole-4-carboxylate i) 2-Amino-5-bromo-thiazole-4-carboxylic acid ethyl ester 2-Amino-thiazole-4-carboxylic acid ethyl ester (1.4 g, 8 mmol) is dissolved in acetonitrile (15 ml) and N-bromosuccinimide. (1.7 g, 9.6 mmol, 1.2 equiv.) was added in one portion. The mixture was stirred at room temp. for 3 hours, then filtered and the filtrate was evaporated. After purification on silica-gel with ethyl acetate/n-heptane as eluent, 0.71 g of an off-white solid were obtained: MS: m/e 248.9 (M–H).

ii) Ethyl 5-bromo-2-({[(3-methylphenyl)sulfonyl]carbamoyl}amino)-1,3-thiazole-4-carboxylate The title compound, MS: m/e 449.9 (M+H) was prepared analogously to the procedure described for Example 64, using toluene-3-sulfonamide and 2-amino-5-bromo-thiazole-4-carboxylic acid ethyl ester.

Example 79

N-[(5-Methoxy-4-methyl-1,3-thiazol-2-yl)carbamoyl]-3-methylbenzenesulfonamide

N-[(5-Bromo-4-methyl-1,3-thiazol-2-yl)carbamoyl]-3-methylbenzenesulfonamide (41 mg, 0.11 mmol) was treated with sodium methanethiolate (31 mg, 0.42 mmol) in methanol (3.1 ml) at 80° C. for 4 days. After purification on preparative HPLC, 9 mg of the title compound were unexpectedly obtained as a white, amorph, freeze-dried solid. MS (ES): m/e 340.1 (M–H)

Example 80

N-{[5-Bromo-4-(hydroxymethyl)-1,3-thiazol-2-yl]carbamoyl}-3-methylbenzenesulfonamide Ethyl 5-bromo-2-({[(3-methylphenyl)sulfonyl]carbamoyl}amino)-1,3-thiazole-4-carboxylate (50 mg, 0.11 mmol) was treated with sodium borohydride (21 mg, 0.56 mmol) in tetrahydrofuran (2 ml) for 2 days at room temp. 0.5 M HCl was added and the quenched reaction mixture was purified on preparative HPLC yielding 21 mg of the title compound as an amorphous solid. MS (ES): m/e 404.1 (M–H)

The title compound, MS: m/e 487.1 (MH⁻), was prepared analogously to the procedure described for Example 11, using 5-(6-methoxy-pyridin-3-yl)-4-methyl-thiophene-2-sulfonic acid amide.

Example A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

It is to be understood that the invention is not limited to the particular embodiments of the invention described above, as variations of the particular embodiments may be made and still fall within the scope of the appended claims.

What is claimed is:

1. A compound of formula (I):

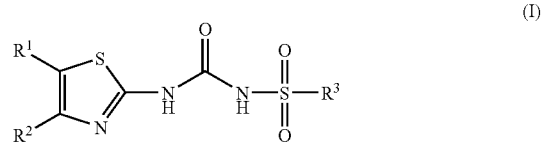

wherein
$R^1$ is alkyl, cycloalkyl, halogen, haloalkyl, heterocyclyl, heterocyclylalkyl, aralkyl, —S—$R^4$, or —O—$R^4$;
$R^2$ is hydrogen, alkyl, cycloalkyl, halogen, haloalkyl, alkoxyalkyl, hydroxyalkyl or alkoxycarbonyl;
or $R^1$ and $R^2$ together with the carbon atoms to which they are attached form aryl;
$R^3$ is phenyl, thiazolyl, thiophenyl, pyridinyl, pyrimidinyl, pyradizinyl, oxazoyl or isoxazoyl, wherein phenyl, thiazolyl, thiophenyl, pyridinyl, pyrimidinyl, pyradizinyl, oxazoyl and isoxazoyl are optionally substituted with one to three substituents independently selected from alkyl, cycloalkyl, alkoxy, hydroxy, halogen, haloalkyl, haloalkoxy, aryl, aryloxy, heterocyclyl, heterocyclyloxy, amino, nitro, alkoxyalkyl, hydroxyalkyl, alkoxyalkoxy and hydroxyalkoxy;

$R^4$ is alkyl, cycloalkyl, heterocyclylalkyl, aralkyl or haloalkyl;

or a pharmaceutically acceptable salt or ester thereof, with the proviso that

N-((2-benzothiazolylamino)carbonyl)-4-methyl-benzenesulfonamide;

N-((2-benzothiazolylamino)carbonyl)-2-methyl-benzenesulfonamide;

N-(((5,6-dimethyl-2-benzothiazolyl)amino)carbonyl)-2-methyl-benzenesulfonamide;

N-(((4-chloro-2-benzothiazolyl)amino)carbonyl)-2-methyl-benzenesulfonamide;

2-methyl-N-(((4-methyl-2-thiazolyl)amino)carbonyl)-benzenesulfonamide;

N-(((6-ethoxy-2-benzothiazolyl)amino)carbonyl)-2-methyl-benzenesulfonamide; and 4-methyl-N-(((4-methyl-2-thiazolyl)amino)carbonyl)-benzenesulfonamide are excluded.

2. The compound according to claim 1, wherein
$R^1$ is alkyl, cycloalkyl, halogen, haloalkyl, heterocyclyl, heterocyclylalkyl, aralkyl, —S—$R^4$ or —O—$R^4$;
$R^2$ is hydrogen, alkyl, cycloalkyl, halogen or haloalkyl;
or $R^1$ and $R^2$ together with the carbon atoms to which they are attached form aryl;
$R^3$ is phenyl, thiazolyl, thiophenyl, pyridinyl, pyrimidinyl, pyradizinyl, oxazoyl or isoxazoyl, wherein phenyl, thiazolyl, thiophenyl, pyridinyl, pyrimidinyl, pyradizinyl, oxazoyl and isoxazoyl are optionally substituted with one to three substituents independently selected from alkyl, cycloalkyl, alkoxy, hydroxy, halogen, haloalkyl, haloalkoxy, aryl, aryloxy, heterocyclyl, heterocyclyloxy, amino and nitro; and
$R^4$ is alkyl, cycloalkyl, heterocyclylalkyl or aralkyl.

3. The compound according to claim 1, wherein $R^1$ is methyl, halogen, thienyl or —S—$R^4$.

4. The compound according to claim 1, wherein $R^1$ is bromo.

5. The compound according to claim 1, wherein $R^2$ is hydrogen, methyl, or halogen.

6. The compound according to claim 1, wherein $R^2$ is hydrogen.

7. The compound according to claim 1, wherein $R^1$ and $R^2$ together with the carbon atoms to which they are attached form phenyl.

8. The compound according to claim 1, wherein $R^3$ is phenyl, thiophenyl, pyridinyl or thiazolyl, wherein phenyl, thiophenyl, pyridinyl and thiazolyl are optionally substituted with one to three substituents independently selected from alkyl, cycloalkyl, halogen, haloalkoxy, alkoxyalkyl, alkoxyalkoxy, aryloxy, dichloro-methyl-1H-pyrazolyl)oxy, methylthiazolyl, cyclohexyl-methyl-oxazolyl, oxazolyl, thiadiazolyl, methyloxazolyl, methylpyrrolidinyl, (methoxymethyl)-pyrrolidinyl, (methylethyl)-pyrrolidinyl, methoxypyridinyl, 6-methoxy-4-methyl-pyridin-3-yl, alkoxy-alkyl-phenyl, alkoxypyridinyl, fluoropyridinyl and methoxy-thiazolyl.

9. The compound according to claim 1, wherein $R^3$ is phenyl, thiophenyl, pyridinyl or thiazolyl, wherein phenyl, thiophenyl, pyridinyl and thiazolyl are optionally substituted with one to three substituents independently selected from alkyl, cycloalkyl, halogen, haloalkoxy, alkoxyalkyl, alkoxyalkoxy, aryloxy, 3,4-dichloro-1-methyl-1H-pyrazol-5-yl)oxy, 2-methyl-4-thiazolyl, 4-cyclohexyl-2-methyl-5-oxazolyl, oxazolyl, 1,2,3-thiadiazol-4-yl, 4-methyl-5-oxazolyl, 2-methyl-1-pyrrolidinyl, 2-(methoxymethyl)-1-pyrrolidinyl, 2-(1-methylethyl)-1-pyrrolidinyl, 6-methoxypyridin-3-yl, 6-methoxy-4-methylpyridin-3-yl, 4-methoxy-2-methylphenyl, methoxy-pyridinyl, 5-isobutyl-4-methylthiophenyl, 6-fluoropyridin-3-yl, 5-fluoropyridin-3-yl and 2-methoxy-1, 3-thiazol-4-yl.

10. The compound according to claim 1, wherein $R^3$ is phenyl, thiophenyl or pyridinyl, wherein phenyl, thiophenyl and pyridinyl are optionally substituted with one to three substituents independently selected from alkyl, cycloalkyl, halogen, haloalkoxy, aryloxy, dichloro-methyl-1H-pyrazolyl)oxy, methylthiazolyl, cyclohexyl-methyl-oxazolyl, oxazolyl, thiadiazolyl, methyloxazolyl, methylpyrrolidinyl, (methoxymethyl)-pyrrolidinyl, (methylethyl)-pyrrolidinyl and methoxypyridinyl.

11. The compound according to claim 1, wherein $R^3$ is phenyl, thiophenyl or pyridinyl, wherein phenyl, thiophenyl and pyridinyl are optionally substituted with one to three substituents independently selected from alkyl, cycloalkyl, halogen, haloalkoxy, aryloxy, 3,4-dichloro-1-methyl-1H-pyrazol-5-yl)oxy, 2-methyl-4-thiazolyl, 4-cyclohexyl-2-methyl-5-oxazolyl, oxazolyl, 1,2,3-thiadiazol-4-yl, 4-methyl-5-oxazolyl, 2-methyl-1-pyrrolidinyl, 2-(methoxymethyl)-1-pyrrolidinyl, 2-(1-methylethyl)-1-pyrrolidinyl and 6-methoxypyridin-3-yl.

12. The compound according to claim 1, wherein $R^3$ is phenyl, thiophenyl or pyridinyl, wherein phenyl, thiophenyl and pyridinyl are optionally substituted with one to three substituents independently selected from alkyl, cyclopropyl, halogen, haloalkoxy, phenyl, difluorophenyl, methylpenyl, methoxyphenyl, methyloxazolyl and methoxypyridinyl.

13. The compound according to claim 1, wherein $R^4$ is alkyl, alkyloxazolylmethyl or phenylmethyl.

14. The compound according to claim 1, wherein $R^4$ is methyl or ((1,1-dimethylethyl)-2-oxazolyl)methyl.

15. The compound according to claim 1, selected from
N-[(5-bromo-1,3-thiazol-2-yl)carbamoyl]3(difluoromethoxy)benzenesulfonamide;
4-bromo-N-[(5-bromo-1,3-thiazol-2-yl)carbamoyl]-5-chlorothiophene-2-sulfonamide;
N-[(5-bromo-1,3-thiazol-2-yl)carbamoyl]-3,4-dichlorobenzenesulfonamide;
N-[(5-bromo-1,3-thiazol-2-yl)carbamoyl]-4-chloro-3-methylbenzenesulfonamide;
N-[(5-bromo-1,3-thiazol-2-yl)carbamoyl]-3-methylbenzenesulfonamide;
N-[(5-bromo-1,3-thiazol-2-yl)carbamoyl]-2',4'-difluorobiphenyl-4-sulfonamide;
N-[(5-bromo-1,3-thiazol-2-yl)carbamoyl]-3-chlorobenzenesulfonamide;
N-[(5-bromo-1,3-thiazol-2-yl)carbamoyl]-4,5-dichlorothiophene-2-sulfonamide;
N-[(5-bromo-1,3-thiazol-2-yl)carbamoyl]-4-(2-chlorophenoxy)-benzenesulfonamide;
N-[(5-bromo-1,3-thiazol-2-yl)carbamoyl]-3,5-dimethylbenzenesulfonamide;
N-[(5-bromo-1,3-thiazol-2-yl)carbamoyl]-4-[(3,4-dichloro -1-methyl-1H-pyrazol-5-yl)oxy]benzenesulfonamide;
N-[(5-bromo-1,3-thiazol-2-yl)carbamoyl]-4-(2-methyl-1, 3-thiazol-4-yl)benzenesulfonamide;
N-[(5-bromo-1,3-thiazol-2-yl)carbamoyl]-5-methylthiophene-2-sulfonamide;
N-[(5-bromo-1,3-thiazol-2-yl)carbamoyl]-5-phenylthiophene-2-sulfonamide;
N-[(5-bromo-1,3-thiazol-2-yl)carbamoyl]biphenyl-4-sulfonamide;

N-[(5-bromo-1,3-thiazol-2-yl)carbamoyl]-5-chlorothiophene-2-sulfonamide;
N-[(5-bromo-1,3-thiazol-2-yl)carbamoyl]-3-fluorobenzenesulfonamide;
N-[(5-bromo-1,3-thiazol-2-yl)carbamoyl]-3-methoxybenzenesulfonamide;
N-[(5-bromo-1,3-thiazol-2-yl)carbamoyl]-2,5-dichlorothiophene-3-sulfonamide;
N-[(5-bromo-1,3-thiazol-2-yl)carbamoyl]-3,4-difluorobenzenesulfonamide;
N-[(5-bromo-1,3-thiazol-2-yl)carbamoyl]-4-methoxybenzenesulfonamide;
N-[(5-bromo-1,3-thiazol-2-yl)carbamoyl]-4-chlorobenzenesulfonamide;
N-[(5-bromo-1,3-thiazol-2-yl)carbamoyl]-4-(4-cyclohexyl-2-methyl-1,3-oxazol-5-yl)-2-fluorobenzenesulfonamide;
N-[(5-bromo-1,3-thiazol-2-yl)carbamoyl]-4-(2-methoxyphenoxy)-benzenesulfonamide;
N-[(5-bromo-1,3-thiazol-2-yl)carbamoyl]-3-nitrobenzenesulfonamide;
N-[(5-bromo-1,3-thiazol-2-yl)carbamoyl]-4-(1,3-oxazol-5-yl)benzenesulfonamide;
N-[(5-bromo-1,3-thiazol-2-yl)carbamoyl]-3,5-difluorobenzenesulfonamide;
N-[(5-bromo-1,3-thiazol-2-yl)carbamoyl]-4-fluorobenzenesulfonamide;
N-[(5-bromo-1,3-thiazol-2-yl)carbamoyl]-4-methylbenzenesulfonamide;
N-[(5-bromo-1,3-thiazol-2-yl)carbamoyl]-4-ethylbenzenesulfonamide;
N-[(5-bromo-1,3-thiazol-2-yl)carbamoyl]benzenesulfonamide;
N-[(5-bromo-1,3-thiazol-2-yl)carbamoyl]-4-(1,2,3-thiadiazol-4-yl)benzenesulfonamide;
N-[(5-bromo-1,3-thiazol-2-yl)carbamoyl]-3-(trifluoromethoxy)-benzenesulfonamide;
N-[(5-{[(5-tert-butyl-1,3-oxazol-2-yl)methyl]thio}-1,3-thiazol-2-yl)carbamoyl]-3-methylbenzenesulfonamide;
3-methyl-N-{[5-(2-thienyl)-1,3-thiazol-2-yl]carbamoyl}benzenesulfonamide;
N-[(4-chloro-1,3-thiazol-2-yl)carbamoyl]-3-methylbenzenesulfonamide;
N-{[5-(benzylthio)-1,3-thiazol-2-yl]carbamoyl}-3-methylbenzenesulfonamide;
N-(1,3-benzothiazol-2-ylcarbamoyl)-3-methylbenzenesulfonamide;
N-[(4,5-dimethyl-1,3-thiazol-2-yl)carbamoyl]-3-methylbenzenesulfonamide;
N-[(5-bromo-1,3-thiazol-2-yl)carbamoyl]-2-ethyl-2'-methylbiphenyl-4-sulfonamide;
N-[(5-bromo-1,3-thiazol-2-yl)carbamoyl]-2-ethylbiphenyl-4-sulfonamide;
N-[(5-bromo-1,3-thiazol-2-yl)carbamoyl]-2-ethyl-3'-methylbiphenyl-4-sulfonamide;
N-[(5-bromo-1,3-thiazol-2-yl)carbamoyl]-2,6-dimethylbiphenyl-4-sulfonamide;
N-[(5-bromo-1,3-thiazol-2-yl)carbamoyl]-4-(4-methyl-1,3-oxazol-5-yl)benzenesulfonamide;
N-[(5-bromo-1,3-thiazol-2-yl)carbamoyl]-5-chloro-6-(2-methylpyrrolidin-1-yl)pyridine-3-sulfonamide;
N-[(5-bromo-1,3-thiazol-2-yl)carbamoyl]-5-chloro-6-[(2S)-2-(methoxymethyl)pyrrolidin-1-yl]pyridine-3-sulfonamide;
N-[(5-bromo-1,3-thiazol-2-yl)carbamoyl]-5-chloro-6-(2-isopropylpyrrolidin-1-yl)pyridine-3-sulfonamide;
N-[(5-bromo-1,3-thiazol-2-yl)carbamoyl]-3-ethylbenzenesulfonamide; ,
N-[(5-bromo-1,3-thiazol-2-yl)carbamoyl]-3-isopropylbenzenesulfonamide;
N-[(5-bromo-1,3-thiazol-2-yl)carbamoyl]-5-(4-methoxyphenyl)thiophene-2-sulfonamide;
N-[(5-bromo-1,3-thiazol-2-yl)carbamoyl]-5-isobutylthiophene-2-sulfonamide;
N-[(5-Bromo-1,3-thiazol-2-yl)carbamoyl]-5-(4-methoxyphenyl)-4-methyl-thiophene-2-sulfonamide;
N-[(5-Chloro-1,3-thiazol-2-yl)carbamoyl]-3-methylbenzenesulfonamide;
3-Chloro-N-{[5-(methylthio)-1,3-thiazol-2-yl]carbamoyl}benzenesulfonamide; and
N-[(5-Bromo-1,3-thiazol-2-yl)carbamoyl]-3cyclopropyl-benzenesulfonamide.

16. The compound according to claim 1, selected from
N-[(5-bromo-1,3-thiazol-2-yl)carbamoyl]-3-(difluoromethoxy)-benzenesulfonamide;
4-bromo-N-[(5-bromo-1,3-thiazol-2-yl)carbamoyl]-5-chlorothiophene-2-sulfonamide;
N-[(5-bromo-1,3-thiazol-2-yl)carbamoyl]-3,4-dichlorobenzenesulfonamide;
N-[(5-bromo-1,3-thiazol-2-yl)carbamoyl]-4-chloro-3-methylbenzenesulfonamide;
N-[(5-bromo-1,3-thiazol-2-yl)carbamoyl]-3-methylbenzenesulfonamide;
N-[(5-bromo-1,3-thiazol-2-yl)carbamoyl]-2',4'-difluorobiphenyl-4-sulfonamide;
N-[(5-{[(5-tert-butyl-1,3-oxazol-2-yl)methyl]thio}-1,3-thiazol-2-yl)carbamoyl]-3-methylbenzenesulfonamide;
N-[(5-bromo-1,3-thiazol-2-yl)carbamoyl]-2-ethyl-2'-methylbiphenyl-4-sulfonamide;
N-[(5-bromo-1,3-thiazol-2-yl)carbamoyl]-2-ethylbiphenyl-4-sulfonamide;
N-[(5-bromo-1,3-thiazol-2-yl)carbamoyl]-4-(4-methyl-1,3-oxazol-5-yl)benzenesulfonamide;
N-[(5-bromo-1,3-thiazol-2-yl)carbamoyl]-3-ethylbenzenesulfonamide;
N-[(5-bromo-1,3-thiazol-2-yl)carbamoyl]-5-(4-methoxyphenyl)thiophene-2-sulfonamide;
N-[(5-bromo-1,3-thiazol-2-yl)carbamoyl]-5-isobutylthiophene-2-sulfonamide;
N-[(5-Bromo-1,3-thiazol-2-yl)carbamoyl]-5-(4-methoxyphenyl)-4-methyl-thiophene-2-sulfonamide;
N-[(5-Chloro-1,3-thiazol-2-yl)carbamoyl]-3-methylbenzenesulfonamide;
3-Chloro-N-{[5-(methylthio)-1,3-thiazol-2-yl]carbamoyl}benzenesulfonamide;
N-[(5-Bromo-1,3-thiazol-2-yl)carbamoyl]-3-cyclopropyl-benzenesulfonamide;
N-[(5-Bromo-1,3-thiazol-2-yl)carbamoyl]-2-chlorobenzenesulfonamide;
N-[(5-Bromo-1,3-thiazol-2-yl)carbamoyl]-5-(6-methoxypyridin-3-yl)-4-methylthiophene-2-sulfonamide; and
N-[(5-bromo-1,3-thiazol-2-yl)carbamoyl]-5-(6-methoxypyridin-3-yl)-4-methylthiophene-2-sulfonamide.

17. The compound according to claim 1, selected from
N-[(5-bromo-1,3-thiazol-2-yl)carbamoyl]-4-chloro-5-(2-methoxyethyl)thiophene-2-sulfonamide;
N-[(5-bromo-1,3-thiazol-2-yl)carbamoyl]-5-(4-methoxy-2-methylphenyl)-4-methylthiophene-2-sulfonamide;
N-[(5-bromo-1,3-thiazol-2-yl)carbamoyl]-4-(6-methoxypyridin-3-yl)-3-methylbenzenesulfonamide;
N-[(5-bromo-1,3-thiazol-2-yl)carbamoyl]-5-isobutyl-4-methylthiophene-2-sulfonamide;

3-methyl-N-({4-methyl-5-[(trifluoromethyl)thio]-1,3-thiazol-2-yl}carbamoyl)benzenesulfonamide;
N-[(5-bromo-1,3-thiazol-2-yl)carbamoyl]-5-(2-methoxyethyl)-4-methylthiophene-2-sulfonamide;
N-[(5-bromo-1,3-thiazol-2-yl)carbamoyl]-4-(6-fluoropyridin-3-yl)-3-methylbenzenesulfonamide;
N-[(5-bromo-1,3-thiazol-2-yl)carbamoyl]-5-(6-fluoropyridin-3-yl)-4-methylthiophene-2-sulfonamide;
N-[(5-bromo-1,3-thiazol-2-yl)carbamoyl]-3-chloro-4-fluorobenzenesulfonamide;
N-[(5-bromo-1,3-thiazol-2-yl)carbamoyl]-5-(3-methoxypropyl)-4-methylthiophene-2-sulfonamide;
N-[(5-bromo-1,3-thiazol-2-yl)carbamoyl]-4-(2-methoxy-1,3-thiazol-4-yl)-3-methylbenzenesulfonamide;
N-[(5-bromo-1,3-thiazol-2-yl)carbamoyl]-4-(5-fluoropyridin -3-yl)-3-methylbenzenesulfonamide;
N-[(5-bromo-1,3-thiazol-2-yl)carbamoyl]-5-methoxy-4-methylthiophene-2-sulfonamide;
N-[(5-bromo-1,3-thiazol-2-yl)carbamoyl]-5-(2-methoxyethoxy)-4-methylthiophene-2-sulfonamide;
N-[(5-bromo-1,3-thiazol-2-yl)carbamoyl]-5-(6-methoxy-4-methylpyridin-3-yl)-4-methylthiophene-2-sulfonamide;
N-[(5-bromo-1,3-thiazol-2-yl)carbamoyl]-5-(methoxymethyl)-4-methylthiophene-2-sulfonamide;
N-[(5-bromo-4-methyl-1,3-thiazol-2-yl)carbamoyl]-3-methylbenzenesulfonamide;
N-[(5-bromo-4-methyl-1,3-thiazol-2-yl)carbamoyl]-3-(difluoromethoxy)benzenesulfonamide;
3-methyl-N-[(4-methyl-5-nitro-1,3-thiazol-2-yl)carbamoyl]benzenesulfonamide;
N-{[5-bromo-4-(methoxymethyl)-1,3-thiazol-2-yl]carbamoyl}-3-methylbenzenesulfonamide;
ethyl 5-bromo-2-({[(3-methylphenyl)sulfonyl]carbamoyl}amino)-1,3-thiazole-4-carboxylate;
N-[(5-methoxy-4-methyl-1,3-thiazol-2-yl)carbamoyl]-3-methylbenzenesulfonamide; and
N-{[5-bromo-4-(hydroxymethyl)-1,3-thiazol-2-yl]carbamoyl}-3-methylbenzenesulfonamide.

18. A process for the preparation of a compound of formula I

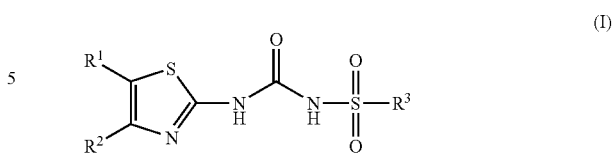

according to claim 1, comprising one of the following steps:
a) reacting a compound according to formula $$R^3-SO_2Cl \qquad II$$

in the presence of NaOCN and a compound of formula

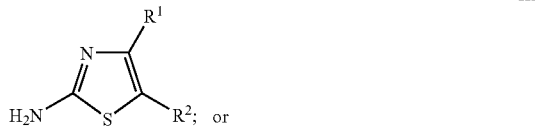

b) reacting a compound according to formula

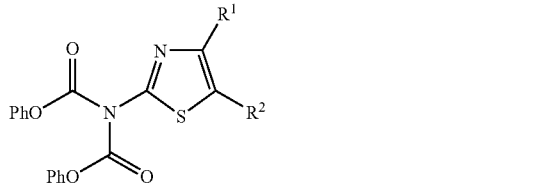

in the presence of a compound of formula $$R^3SO_2NH_2 \qquad VI;$$

wherein $R^1$ to $R^3$ are defined according to claim 1.

19. A pharmaceutical composition, comprising a therapeutically effective amount of a compound according to claim 1 and a therapeutically inert carrier.

* * * * *